US007468425B2

(12) United States Patent
Sidransky et al.

(10) Patent No.: US 7,468,425 B2
(45) Date of Patent: Dec. 23, 2008

(54) *P40* PROTEIN ACTS AS AN ONCOGENE

(75) Inventors: David Sidransky, Baltimore, MD (US); Jin Jen, Brookeville, MD (US); Barry Trink, Baltimore, MD (US); Edward A. Ratovitski, Columbia, MD (US)

(73) Assignee: The Johns Hopkins University, Baltimore, MD (US)

( * ) Notice: Subject to any disclaimer, the term of this patent is extended or adjusted under 35 U.S.C. 154(b) by 282 days.

(21) Appl. No.: 10/274,874

(22) Filed: Oct. 22, 2002

(65) Prior Publication Data

US 2003/0113774 A1 Jun. 19, 2003

Related U.S. Application Data

(62) Division of application No. 09/277,196, filed on Mar. 26, 1999, now Pat. No. 6,476,206.

(60) Provisional application No. 60/079,736, filed on Mar. 27, 1998.

(51) Int. Cl.
*C07K 5/00* (2006.01)
(52) U.S. Cl. ................................... 530/387.1
(58) Field of Classification Search ............... 530/387.1, 530/350; 424/130.1, 9.1
See application file for complete search history.

(56) References Cited

U.S. PATENT DOCUMENTS

| | | | | |
|---|---|---|---|---|
| 6,451,979 | B1 * | 9/2002 | Kaelin et al. | 530/387.1 |
| 6,946,256 | B1 * | 9/2005 | McKeon et al. | 435/7.1 |
| 2005/0202016 | A1 * | 9/2005 | Caput et al. | 424/146.1 |

FOREIGN PATENT DOCUMENTS

| EP | 0 710 722 A | 5/1996 |
|---|---|---|
| WO | 97/28186 A | 8/1997 |
| WO | 99/19357 A | 4/1999 |

OTHER PUBLICATIONS

Cruse et al., Illustrated Dictionary of Immunology, 1995 by CRC press, p. 241.*
Schmale et al. "KET protein" EMBL Sequence Database, Jan. 1, 1998 XP002113673 Heidelberg DE.
Schmale et al., "A Novel protein with strong homology to the tumor suppressor p53" Oncogene, vol. 15, No. 11, Sep. 1997 pp. 1363-1367.
A. Yang et al. "p63, a p53 homolog at 3q27-29, encodes multiple products with transactivating, death inducing, and dominant-negative activities" Molecular Cell, vol. 2, No. 3, Sep. 1993, pp. 305-316.
Trink et al., "*Homo sapiens* p53 homolog (p40) mRNA, complete eds" EMBL Sequence Database, Jul. 1, 1998 XP002113674 Heidelberg DE.
Trink et al., "A new human p53 homologue" NatureMedicine, vol. 4, No. 7, Jul. 1998, pp. 747-748.
Carol Prives "Signaling to p53: Breaking the MDM2-p53 Circuit" Cell, vol. 95, 5-8 Oct. 2, 1998.
Hansen and Oren "p53: from inductive signal to cellular effect" Current Opinion in Genetics & Development 1997, 7:46-51.
Senoo et al., BBRC vol. 248, p. 603.
GenBank Accession No. AF061512.

* cited by examiner

*Primary Examiner*—Christopher H. Yaen
*Assistant Examiner*—Hong Sang
(74) *Attorney, Agent, or Firm*—Banner & Witcoff, Ltd.

(57) ABSTRACT

We have discovered p40, the shortest variant of a new human p53 homologue (p40/p51/p63/p73H). We have also found that it plays a role in cancer. Low level amplification of the p40 locus accompanied by RNA and protein overexpression was observed in primary lung cancers, and head and neck cancer cell lines. P40 protein overexpression in primary lung tumors was limited to squamous cell carcinoma, tumors known to harbor a high frequency of p53 mutations. Overexpression of p40 in Rat 1a cells led to an increase in soft agar growth and tumor size in mice. We searched for p40 binding proteins using the yeast two-hybrid system. P53 was the most common binding target of the $1.6 \times 10^6$ clones screened from a mouse embryonic library. Moreover, coexpression of p40 and p53 led to a decrease in p53 transcriptional activity. Our results support the notion that p40 plays an oncogenic role in human cancer.

3 Claims, 11 Drawing Sheets

(5 of 11 Drawing Sheet(s) Filed in Color)

FIG. 6a

```
            1                15 16             30 31             45 46             60 61             75 76             90
p53         ----------------  ---------------- ---------------- ----MEEPQSDPS -VEPPLSQETFSDLW KLLPENNVLSPLPSQ AMDDLMLSPDDIEQW   53
p73α        MAQSTATSPDGGTTF  EHLWSSLE-P-----  ---------DSTYFDLPQSSRG NNEVVGGTDSSMDVF HLEG--MTTSVMAQF N---LLSSTMDQMSS         77
ket         ---SEFLSPE---VF  QHIWDFLEQPICSVQ  PIDLNFVDEP-SENG  ---------------- ATNKIEISMDCI RMQDSDLSDPMWPQY TNLGLLNGMDQQIQN    80
p40         ---------------  ---------------- ---------------- ---------------- ---------ML YLENNAQTQFSEPQY TNLGLLNSMDQQIQN    32

91              105 106           120 121           135 136           150 151           165 166           180
p53         FTEDPGDEAPRMPE   AAPRVAPAPAAPTPA  APAPAPSWPLSSSVP  SQKTYQGSYGFRLGF  ---------------- ---------------- ALNKMFCQLAKTCPV  143
p73α        RAASASPYTPEHAA-  SVPTHSPYAQ-PSST  FDTMSP-----APVIP SNTDYPGPHHFEVTF  ---------------- ---------------- LLKKLYCQIAKTCPI  161
ket         GSSSTSPYNTDHAQN  SVTAPSPYAQ-PSST  FDALSP----SPAIP  SNTDYPGPHSFDVSF  QQSSTAKSATWTYST  ---------------- ELKKLYCQIAKTCPI  165
p40         GSSSTSPYNTDHAQN  SVTAPSPYAQ-PSST  FDALSP----SPAIP  SNTDYPGPHSFDVSF  QQSSTAKSATWTYST  ---------------- ELKKLYCQIAKTCPI  117

181             195 196           210 211           225 226           240 241           255 256           270
p53         QLWVDSTPPPGTRVR  AMAIYKQSQHMTEVV  RCPHHERCSDSD-G   -LAPPQHLIRVEGNL  RVEYLDDRNTFRHSV  VVPYEPPEVGSDCTT                   231
p73α        QIKVSTPPPPGTAIR  AMPVYKKAEHVTDVV  KRCPNHELGRDFNEG  QSAPASHLIRVEGNN  LSQYVDDPVTGRQSV  VVPYEPPOVGTEFTT                   251
ket         QIKVMTPPPQGAVIR  AMPVYKKAEHVTEVV  KRCPNHELSREFNEG  QIAPPSHLIRVEGNS  HAQYVEDPITGRQSV  LVPYEPPOVGTEFTT                   255
p40         QIKVMTPPPQGAVIR  AMPVYKKAEHVTEVV  KRCPNHELSREFNEG  QIAPPSHLIRVEGNS  HAQYVEDPITGRQSV  LVPYEPPOVGTEFTT                   207

271             285 286           300 301           315 316           330 331           345 346           360
p53         THYNYMCNSSCMGGM  NRRPILTIITLEDSS  GNLLGRNSFEVRVCA  CPGRDRRTEENLRK   KG--EPHHELPPGST  KRALPNNTSSSPQP-                   318
p73α        ILYNFMCNSSCMGGM  NRRPILTIITLTLEMRD GQVLGRRSFEGRICA CPGRDRKADEDHYRE  QQALNESSAKNGAAS  KRAFKQSPPAVPALG                   341
ket         VLYNFMCNSSCVGGM  NRRPILLIIVTLETRD GQVLGRRCFEARICA CPGRDRKADEDSIRK  QQ-VSDS-AKNGDGT  KRPFRQNTHGIQMT-                   342
p40         VLYNFMCNSSCVGGM  NRRPILLIIVTLETRD GQVLGRRCFEARICA CPGRDRKADEDSIRK  QQ-VSDS-TKNGDGT  KRPSRQNTHGIQMT-                   294

361             375 376           390 391           405 406           420 421           435 436           450
p53         ---K-KPLDGEYFT   LQIRGRERFEMFREL NEALELKDAQAGKEP  GGSRAHSS----HLK  SKKGQSTSRHKKLMF  KTEGPDSD-------                   393
p73α        AGVKKRRHGDEDTYY  LQVRGRENFEILMKL  KESLELMQYLPQPLV  DSYRQQQQ----LL  QRPSHLQPPS-YGPV  LSPMNKVH-//--IH                   636
ket         -SIKKRRSPDDELLY  LPVRGRETYEMLLKI  KESLELMQYLPQHTI  ETYRQQQQQHQHLL  QKQTSMQSQSSYGNS  SPPLNKMN-//-GE                    634
p40         -SIKKRRSPDDELLY  LPVRGRETYEMLLKI  KESLELMQYLPQHTI  ETYRQQQQQHQHLL  QKQ------------- ---------------                   356
```

*FIG. 7a*  *FIG. 7b*
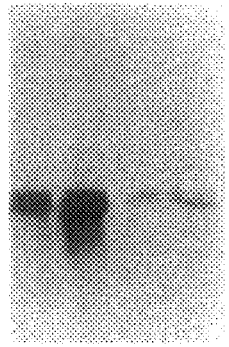

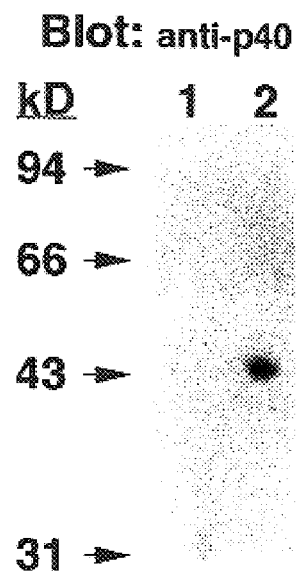 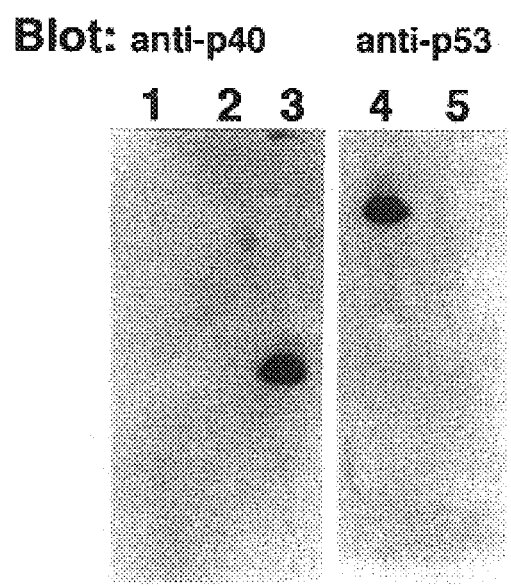
FIG. 8a
FIG. 8b

SEQUENCE LISTING

```
<160> NUMBER OF SEQ ID NOS: 20

<210> SEQ ID NO 1
<211> LENGTH: 2082
<212> TYPE: DNA
<213> ORGANISM: Homo sapiens

<400> SEQUENCE: 1
agatgctaca gcgactgcac acccaggctg tatgatacag cctattgctc ccgggctgca      60
aacctgtcca gcatgtgatg tggtgggata ctgaattgaa taccgaatac tgtaggcaat     120
tgtaacacag tggtaagtct ttgtgtatct aaacatagct aaacaccaaa aggtatagta     180
agaatatggt attataatct tatggaacta tcattgtata tgtggtttgt caaccagaat     240
gtagttatac agcacaggac tgtgcttatg atgtgccaag cacagctctc agtactaact     300
cctttaatct tcatatcaac cctaggaggt aacttcttaa gtagattcat attgtaaggg     360
tctcggggtg gggggttgg caaaatcctg gagccagaag aaaggacagc agcattgatc      420
aatcttacag ctaacatgtt gtacctggaa aacaatgccc agactcaatt tagtgagcca     480
cagtacacga acctggggct cctgaacagc atggaccagc agattcagaa cggctcctcg     540
tccaccagtc cctataacac agaccacgcg cagaacagcg tcacggcgcc ctcgccctac     600
gcacagccca gctccacctt cgatgctctc tctccatcac ccgccatccc ctccaacacc     660 gactaccag gcccgcacag tttcgacgtg tccttccagc agtcgagcac cgccaagtcg     720
gccacctgga cgtattccac tgaactgaag aaactctact gccaaattgc aaagacatgc     780
cccatccaga tcaaggtgat gacccccacct cctcagggag ctgttatccg cgccatgcct     840
gtctacaaaa aagctgagca cgtcacggag gtggtgaagc ggtgccccaa ccatgagctg     900
```

```
agccgtgaat tcaacgaggg acagattgcc cctcctagtc atttgattcg agtagagggg    960
aacagccatg cccagtatgt agaagatccc atcacaggaa gacagagtgt gctggtacct   1020
tatgagccac cccaggttgg cactgaattc acgacagtct tgtacaattt catgtgtaac   1080
agcagttgtg ttggagggat gaaccgccgt ccaattttaa tcattgttac tctggaaacc   1140
agagatgggc aagtcctggg ccgacgctgc tttgaggccc ggatctgtgc ttgcccagga   1200
agagacagga aggcggatga agatagcatc agaaagcagc aagtttcgga cagtacaaag   1260
aacggtgatg gtacgaagcg cccgtctcgt cagaacacac atggtatcca gatgacatcc   1320
atcaagaaac gaagatcccc agatgatgaa ctgttatact taccagtgag gggccgtgag   1380
acttatgaaa tgctgttgaa gatcaaagag tccctggaac tcatgcagta ccttcctcag   1440
cacacaattg aaacgtacag gcaacagcaa cagcagcagc accagcactt acttcagaaa   1500
cagtgagtgt atcaacgtgt cattttagga ggcatgagtg acggtgactt tatttggatc   1560
agcaataggg tgattgatga gcaatgtgga acataatggg agatagcaga ttgtcataga   1620
ttcagatgac ctggtatggc aaccctcttt cagttgcaac cttttttacg tgtcttatta   1680
taaccttccc ttcagaattc cacttatgtt ctgaaattaa atacaaacca tttctggtga   1740
attacaaaga aactcacact aacagttctc ttctctatat gcctggtcca tacacactaa   1800
cagtaagtac acactctatt tggtagtgat gtgtatattt gaaaacatga aatcttttct   1860
catcccaatg gattgtctta taaatctcct gggatgcaca ctatccactt tgggaataa    1920
cactgtagac cagggatagc aaataggctt tactataata taaagtgact tgtttgaatg   1980
ctgtaatgag aagaattctg agacctagtg catgataatt ggggaaatat ctgggtgcag   2040
aaggataagg tagcatcatg ttgccgtatt ttagcatctc tg                      2082
```

<210> SEQ ID NO 2
<211> LENGTH: 356
<212> TYPE: PRT
<213> ORGANISM: Homo sapiens

<400> SEQUENCE: 2

```
Met Leu Tyr Leu Glu Asn Asn Ala Gln Thr Gln Phe Ser Glu Pro Gln
  1               5                  10                  15

Tyr Thr Asn Leu Gly Leu Leu Asn Ser Met Asp Gln Gln Ile Gln Asn
                 20                  25                  30

Gly Ser Ser Ser Thr Ser Pro Tyr Asn Thr Asp His Ala Gln Asn Ser
             35                  40                  45

Val Thr Ala Pro Ser Pro Tyr Ala Gln Pro Ser Ser Thr Phe Asp Ala
         50                  55                  60

Leu Ser Pro Ser Pro Ala Ile Pro Ser Asn Thr Asp Tyr Pro Gly Pro
 65                  70                  75                  80

His Ser Phe Asp Val Ser Phe Gln Gln Ser Ser Thr Ala Lys Ser Ala
                 85                  90                  95

Thr Trp Thr Tyr Ser Thr Glu Leu Lys Lys Leu Tyr Cys Gln Ile Ala
                100                 105                 110

Lys Thr Cys Pro Ile Gln Ile Lys Val Met Thr Pro Pro Gln Gly
            115                 120                 125

Ala Val Ile Arg Ala Met Pro Val Tyr Lys Lys Ala Glu His Val Thr
        130                 135                 140

Glu Val Val Lys Arg Cys Pro Asn His Glu Leu Ser Arg Glu Phe Asn
145                 150                 155                 160

Glu Gly Gln Ile Ala Pro Pro Ser His Leu Ile Arg Val Glu Gly Asn
```

```
                165                 170                 175
Ser His Ala Gln Tyr Val Glu Asp Pro Ile Thr Gly Arg Gln Ser Val
                    180                 185                 190

Leu Val Pro Tyr Glu Pro Pro Gln Val Gly Thr Glu Phe Thr Thr Val
                195                 200                 205

Leu Tyr Asn Phe Met Cys Asn Ser Ser Cys Val Gly Met Asn Arg
            210                 215                 220

Arg Pro Ile Leu Ile Ile Val Thr Leu Glu Thr Arg Asp Gly Gln Val
225                 230                 235                 240

Leu Gly Arg Arg Cys Phe Glu Ala Arg Ile Cys Ala Cys Pro Gly Arg
                245                 250                 255

Asp Arg Lys Ala Asp Glu Asp Ser Ile Arg Lys Gln Gln Val Ser Asp
                260                 265                 270

Ser Thr Lys Asn Gly Asp Gly Thr Lys Arg Pro Ser Arg Gln Asn Thr
                275                 280                 285

His Gly Ile Gln Met Thr Ser Ile Lys Lys Arg Arg Ser Pro Asp Asp
                290                 295                 300

Glu Leu Leu Tyr Leu Pro Val Arg Gly Arg Glu Thr Tyr Glu Met Leu
305                 310                 315                 320

Leu Lys Ile Lys Glu Ser Leu Glu Leu Met Gln Tyr Leu Pro Gln His
                325                 330                 335

Thr Ile Glu Thr Tyr Arg Gln Gln Gln Gln Gln Gln His Gln His Leu
                340                 345                 350

Leu Gln Lys Gln
        355

<210> SEQ ID NO 3
<211> LENGTH: 2065
<212> TYPE: DNA
<213> ORGANISM: Homo sapiens

<400> SEQUENCE: 3
caaaacctac cagggcagct accgtttccg tctgggcttc ttgcattctg ggacagccaa      60
gtctgtgact tgcacgtact cccctgccct caacaagatg ttttgccaac tggccaagac     120
ctgcccctgt gcagctgtgg gttgattcca ccccccgccc ggcacccgcg tccgcgccat     180
ggccatctac aagcagtcac agcacatgac ggaggttgtg aggcgctgcc cccaccatga     240
gcgctgctca gatagcgatg gtctggcccc tcctcagcat cttatccgag tggaaggaaa     300
tttgcgtgtg gagtatttgg atgacagaaa cacttttcga catagtgtgg tggtgcccta     360
tgagccgcct gaggaggttg gctctgactg taccaccatc cactacaact acatgtgtaa     420
cagttcctgc atgggcggca tgaaccggag gcccatcctc accatcatca cactggaaga     480
ctccagtggt aatctactgg gacggaacag ctttgaggtg cgtgtttgtg cctgtcctgg     540
gagagaccgg cgcacagagg aagagaatct ccgcaagaaa gggagcctca ccacgagct     600
gcccccaggg agcactaagc gagcactgcc aacaacacc agctcctctc cccagccaaa     660
gaagaaacca ctggatggag aatatttcac ccttcgatc cgtgggcgtg agcgcttcga     720
gatgttccga gagctgaatg aggccttgga actcaaggat gcccaggctg gaaggagcc     780
aggggggagc agggctcact ccagccacct gaagtccaaa aaggctcagt ctacctcccg     840
ccataaaaaa ctcatgttca agacagaagg gcctgactca gactgacatt ctccacttct     900
tgttccccac tgcagcctc ccacccccat ctctccctcc cctgccattt gggttttgg     960
gtctttgaac ccttgcttgc aataggtgtg cgtcagaagc acccaggact tccatttgct    1020
```

-continued

```
ttgtcccggg gctccactga acaagttggc ctgcactgct gttttgttgt ggggaggagg      1080
atggggagta ggacatacca gcttagattt taaggttttt actgtgaggg atgtttggga      1140
gatgtaagaa atgttcttgc agttaagggt tagtttacaa tcagccacat tctaggtagg      1200
ggcccacttc accgtactaa ccagggaagc tgtccctcac tgttgaattt tctctaactt      1260
caaggcccat atctgtgaaa tgctggcatt tgcacctacc tcacagagtg cattgtgagg      1320
gttaatgaaa taatgtacat ctggccttga aaccaccttt tattacatgg ggtctagatg      1380
acccccttga ggtgcttgtt ccctctccct gttggtcggt gggttggtag tttctacagt      1440
tgggcagctg gttaggtaga gggagttgtc aagtctctgc tggcccagcc aaaccctgtc      1500
tgacaacctc ttggtgaacc ttagatccta aaaggaaatg tcaccccatc ccacaccctg      1560
gaggatttca tctcttgtat agatgatctg gatccaccaa gacttgttgt tttagctcag      1620
ggtccaattt ctttttttctt tttttttttt ttttctttt tctttgagac tgggtctctt      1680
tgttgcccca ggctggagtg gagtggcgtg atctggctta ctgcagcctt tgcctccccg      1740
gctcgagcag tcctgcctca gcctccggag tagctgggac cacaggttca tgccaccatg      1800
gccagccaac ttttgcatgt tttgtagaga tggggtctca cagtgttgcc caggctggtc      1860
tcaaactcct gggctcaggc gatccacctg tctcagcctc ccagagtggg attacaattg      1920
tgagccacca cgtccagctg aagggtcaa catcttttac attctgcaag cacatctgca      1980 ttttcaccccc acccttcccc tcttctcccct ttttatatcc cattttata tcgatctctt      2040 attttacaat aaaactttgc tgcca                                              2065
```

<210> SEQ ID NO 4
<211> LENGTH: 393
<212> TYPE: PRT
<213> ORGANISM: Homo sapiens

<400> SEQUENCE: 4

```
Met Glu Glu Pro Gln Ser Asp Pro Ser Val Glu Pro Pro Leu Ser Gln
 1               5                  10                  15

Glu Thr Phe Ser Asp Leu Trp Lys Leu Leu Pro Glu Asn Asn Val Leu
            20                  25                  30

Ser Pro Leu Pro Ser Gln Ala Met Asp Asp Leu Met Leu Ser Pro Asp
        35                  40                  45

Asp Ile Glu Gln Trp Phe Thr Glu Asp Pro Gly Pro Asp Glu Ala Pro
    50                  55                  60

Arg Met Pro Glu Ala Ala Pro Arg Val Ala Pro Ala Pro Ala Ala Pro
65                  70                  75                  80

Thr Pro Ala Ala Pro Ala Pro Ala Pro Ser Trp Pro Leu Ser Ser Ser
                85                  90                  95

Val Pro Ser Gln Lys Thr Tyr Gln Gly Ser Tyr Gly Phe Arg Leu Gly
            100                 105                 110

Phe Leu His Ser Gly Thr Ala Lys Ser Val Thr Cys Thr Tyr Ser Pro
        115                 120                 125

Ala Leu Asn Lys Met Phe Cys Gln Leu Ala Lys Thr Cys Pro Val Gln
    130                 135                 140

Leu Trp Val Asp Ser Thr Pro Pro Gly Thr Arg Val Arg Ala Met Ala
145                 150                 155                 160

Ala Ile Tyr Lys Gln Ser Gln His Met Thr Glu Val Val Arg Arg Cys
                165                 170                 175

Pro His His Glu Arg Cys Ser Asp Ser Asp Gly Leu Ala Pro Pro Gln
```

```
                180             185             190
His Leu Ile Arg Val Glu Gly Asn Leu Arg Val Glu Tyr Leu Asp Asp
            195                 200                 205

Arg Asn Thr Phe Arg His Ser Val Val Pro Tyr Glu Pro Pro Glu
    210                 215                 220

Val Gly Ser Asp Cys Thr Thr Ile His Tyr Asn Tyr Met Cys Asn Ser
225                 230                 235                 240

Ser Cys Met Gly Gly Met Asn Arg Arg Pro Ile Leu Thr Ile Ile Thr
                245                 250                 255

Leu Glu Asp Ser Ser Gly Asn Leu Leu Gly Arg Asn Ser Phe Glu Val
            260                 265                 270

Arg Val Cys Ala Cys Pro Gly Arg Asp Arg Arg Thr Glu Glu Glu Asn
                275                 280                 285

Leu Arg Lys Lys Gly Glu Pro His His Glu Leu Pro Pro Gly Ser Thr
            290                 295                 300

Lys Arg Ala Leu Pro Asn Asn Thr Ser Ser Ser Pro Gln Pro Lys Lys
305                 310                 315                 320

Lys Pro Leu Asp Gly Glu Tyr Phe Thr Leu Gln Ile Arg Gly Arg Glu
                325                 330                 335

Arg Phe Glu Met Phe Arg Glu Leu Asn Glu Ala Leu Glu Leu Lys Asp
                340                 345                 350

Ala Gln Ala Gly Lys Glu Pro Gly Gly Ser Arg Ala His Ser Ser His
            355                 360                 365

Leu Lys Ser Lys Lys Gly Gln Ser Thr Ser Arg His Lys Lys Leu Met
            370                 375                 380

Phe Lys Thr Glu Gly Pro Asp Ser Asp
385                 390

<210> SEQ ID NO 5
<211> LENGTH: 22
<212> TYPE: DNA
<213> ORGANISM: Homo sapiens

<400> SEQUENCE: 5
gcagcattga tcaatcttac ag                                                22

<210> SEQ ID NO 6
<211> LENGTH: 21
<212> TYPE: DNA
<213> ORGANISM: Homo sapiens

<400> SEQUENCE: 6
tgaattcacg gctcagctca t                                                 21

<210> SEQ ID NO 7
<211> LENGTH: 21
<212> TYPE: DNA
<213> ORGANISM: Homo sapiens

<400> SEQUENCE: 7
cgccatgcct gtctacaaaa a                                                 21

<210> SEQ ID NO 8
<211> LENGTH: 21
<212> TYPE: DNA
<213> ORGANISM: Homo sapiens

<400> SEQUENCE: 8
```

-continued

| | |
|---|---|
| gcctcctaaa atgacacgtt g | 21 |

<210> SEQ ID NO 9
<211> LENGTH: 20
<212> TYPE: DNA
<213> ORGANISM: Homo sapiens

<400> SEQUENCE: 9

| | |
|---|---|
| gccacagtac acgaacctgg | 20 |

<210> SEQ ID NO 10
<211> LENGTH: 21
<212> TYPE: DNA
<213> ORGANISM: Homo sapiens

<400> SEQUENCE: 10

| | |
|---|---|
| cgtggtctgt gttataggga c | 21 |

<210> SEQ ID NO 11
<211> LENGTH: 20
<212> TYPE: DNA
<213> ORGANISM: Homo sapiens

<400> SEQUENCE: 11

| | |
|---|---|
| tgtccttcca gcagtcgagc | 20 |

<210> SEQ ID NO 12
<211> LENGTH: 20
<212> TYPE: DNA
<213> ORGANISM: Homo sapiens

<400> SEQUENCE: 12

| | |
|---|---|
| aaaagctgag cacgtcacgg | 20 |

<210> SEQ ID NO 13
<211> LENGTH: 20
<212> TYPE: DNA
<213> ORGANISM: Homo sapiens

<400> SEQUENCE: 13

| | |
|---|---|
| cttcaccacc tccgtgacgt | 20 |

<210> SEQ ID NO 14
<211> LENGTH: 21
<212> TYPE: DNA
<213> ORGANISM: Homo sapiens

<400> SEQUENCE: 14

| | |
|---|---|
| aggttggcac tgaattcacg a | 21 |

<210> SEQ ID NO 15
<211> LENGTH: 20
<212> TYPE: DNA
<213> ORGANISM: Homo sapiens

<400> SEQUENCE: 15

| | |
|---|---|
| aaaattggac ggcggttcat | 20 |

<210> SEQ ID NO 16
<211> LENGTH: 19
<212> TYPE: DNA
<213> ORGANISM: Homo sapiens

<400> SEQUENCE: 16

```
gtgatggtac gaagcgccc                                                        19
```

<210> SEQ ID NO 17
<211> LENGTH: 18
<212> TYPE: DNA
<213> ORGANISM: Homo sapiens

<400> SEQUENCE: 17

```
acgggcgctt cgtaccat                                                         18
```

<210> SEQ ID NO 18
<211> LENGTH: 13
<212> TYPE: PRT
<213> ORGANISM: Homo sapiens

<400> SEQUENCE: 18

Glu Asn Asn Ala Gln Thr Gln Phe Ser Glu Pro Gln Tyr
 1               5                  10

<210> SEQ ID NO 19
<211> LENGTH: 426
<212> TYPE: PRT
<213> ORGANISM: Homo sapiens

<400> SEQUENCE: 19

Ser Glu Phe Leu Ser Pro Glu Val Phe Gln His Ile Trp Asp Phe Leu
 1               5                  10                  15

Glu Gln Pro Ile Cys Ser Val Gln Pro Ile Asp Leu Asn Phe Val Asp
                20                  25                  30

Glu Pro Ser Glu Asn Gly Ala Thr Asn Lys Ile Glu Ile Ser Met Asp
            35                  40                  45

Cys Ile Arg Met Gln Asp Ser Asp Leu Ser Asp Pro Met Trp Pro Gln
        50                  55                  60

Tyr Thr Asn Leu Gly Leu Leu Asn Gly Met Asp Gln Gln Ile Gln Asn
 65                  70                  75                  80

Gly Ser Ser Ser Thr Ser Pro Tyr Asn Thr Asp His Ala Gln Asn Ser
                85                  90                  95

Val Thr Ala Pro Ser Pro Tyr Ala Gln Pro Ser Ser Thr Phe Asp Ala
                100                 105                 110

Leu Ser Pro Ser Pro Ala Ile Pro Ser Asn Thr Asp Tyr Pro Gly Pro
            115                 120                 125

His Ser Phe Asp Val Ser Phe Gln Gln Ser Ser Thr Ala Lys Ser Ala
        130                 135                 140

Thr Trp Thr Tyr Ser Thr Glu Leu Lys Lys Leu Tyr Cys Gln Ile Ala
145                 150                 155                 160

Lys Thr Cys Pro Ile Gln Ile Lys Val Met Thr Pro Pro Gln Gly
                165                 170                 175

Ala Val Ile Arg Ala Met Pro Val Tyr Lys Lys Ala Glu His Val Thr
            180                 185                 190

Glu Val Val Lys Arg Cys Pro Asn His Glu Leu Ser Arg Glu Phe Asn
        195                 200                 205

Glu Gly Gln Ile Ala Pro Pro Ser His Leu Ile Arg Val Glu Gly Asn
    210                 215                 220

Ser His Ala Gln Tyr Val Glu Asp Pro Ile Thr Gly Arg Gln Ser Val
225                 230                 235                 240

Leu Val Pro Tyr Glu Pro Pro Gln Val Gly Thr Glu Phe Thr Thr Val
                245                 250                 255

```
Leu Tyr Asn Phe Met Cys Asn Ser Ser Cys Val Gly Gly Met Asn Arg
            260                 265                 270

Arg Pro Ile Leu Ile Val Thr Leu Glu Thr Arg Asp Gly Gln Val
        275                 280                 285

Leu Gly Arg Arg Cys Phe Glu Ala Arg Ile Cys Ala Cys Pro Gly Arg
            290                 295                 300

Asp Arg Lys Ala Asp Glu Asp Ser Ile Arg Lys Gln Gln Val Ser Asp
305                 310                 315                 320

Ser Ala Lys Asn Gly Asp Gly Thr Lys Arg Pro Phe Arg Gln Asn Thr
                325                 330                 335

His Gly Ile Gln Met Thr Ser Ile Lys Lys Arg Arg Ser Pro Asp Asp
            340                 345                 350

Glu Leu Leu Tyr Leu Pro Val Arg Gly Arg Glu Thr Tyr Glu Met Leu
            355                 360                 365

Leu Lys Ile Lys Glu Ser Leu Glu Leu Met Gln Tyr Leu Pro Gln His
        370                 375                 380

Thr Ile Glu Thr Tyr Arg Gln Gln Gln Gln Gln His Gln His Leu
385                 390                 395                 400

Leu Gln Lys Gln Thr Ser Met Gln Ser Gln Ser Ser Tyr Gly Asn Ser
                405                 410                 415

Ser Pro Pro Leu Asn Lys Met Asn Gly Glu
            420                 425

<210> SEQ ID NO 20
<211> LENGTH: 420
<212> TYPE: PRT
<213> ORGANISM: Homo sapiens

<400> SEQUENCE: 20

Met Ala Gln Ser Thr Ala Thr Ser Pro Asp Gly Gly Thr Thr Phe Glu
1               5                   10                  15

His Leu Trp Ser Ser Leu Glu Pro Asp Ser Thr Tyr Phe Asp Leu Pro
            20                  25                  30

Gln Ser Ser Arg Gly Asn Asn Glu Val Val Gly Gly Thr Asp Ser Ser
        35                  40                  45

Met Asp Val Phe His Leu Glu Gly Met Thr Thr Ser Val Met Ala Gln
    50                  55                  60

Phe Asn Leu Leu Ser Ser Thr Met Asp Gln Met Ser Ser Arg Ala Ala
65                  70                  75                  80

Ser Ala Ser Pro Tyr Thr Pro Glu His Ala Ala Ser Val Pro Thr His
                85                  90                  95

Ser Pro Tyr Ala Gln Pro Ser Ser Thr Phe Asp Thr Met Ser Pro Ala
            100                 105                 110

Pro Val Ile Pro Ser Asn Thr Asp Tyr Pro Gly Pro His His Phe Glu
        115                 120                 125

Val Thr Phe Gln Gln Ser Ser Thr Ala Lys Ser Ala Thr Trp Thr Tyr
    130                 135                 140

Ser Pro Leu Leu Lys Lys Leu Tyr Cys Gln Ile Ala Lys Thr Cys Pro
145                 150                 155                 160

Ile Gln Ile Lys Val Ser Thr Pro Pro Pro Gly Thr Ala Ile Arg
                165                 170                 175

Ala Met Pro Val Tyr Lys Lys Ala Glu His Val Thr Asp Val Val Lys
            180                 185                 190

Arg Cys Pro Asn His Glu Leu Gly Arg Asp Phe Asn Glu Gly Gln Ser
```

-continued

```
                195                 200                 205
Ala Pro Ala Ser His Leu Ile Arg Val Glu Gly Asn Asn Leu Ser Gln
    210                 215                 220

Tyr Val Asp Asp Pro Val Thr Gly Arg Gln Ser Val Val Val Pro Tyr
225                 230                 235                 240

Glu Pro Pro Gln Val Gly Thr Glu Phe Thr Thr Ile Leu Tyr Asn Phe
                245                 250                 255

Met Cys Asn Ser Ser Cys Val Gly Gly Met Asn Arg Arg Pro Ile Leu
                260                 265                 270

Ile Ile Ile Thr Leu Glu Met Arg Asp Gly Gln Val Leu Gly Arg Arg
                275                 280                 285

Ser Phe Glu Gly Arg Ile Cys Ala Cys Pro Gly Arg Asp Arg Lys Ala
    290                 295                 300

Asp Glu Asp His Tyr Arg Glu Gln Gln Ala Leu Asn Glu Ser Ser Ala
305                 310                 315                 320

Lys Asn Gly Ala Ala Ser Lys Arg Ala Phe Lys Gln Ser Pro Pro Ala
                325                 330                 335

Val Pro Ala Leu Gly Ala Gly Val Lys Lys Arg Arg His Gly Asp Glu
                340                 345                 350

Asp Thr Tyr Tyr Leu Gln Val Arg Gly Arg Glu Asn Phe Glu Ile Leu
                355                 360                 365

Met Lys Leu Lys Glu Ser Leu Glu Leu Met Glu Leu Val Pro Gln Pro
    370                 375                 380

Leu Val Asp Ser Tyr Arg Gln Gln Gln Gln Leu Leu Gln Arg Pro Ser
385                 390                 395                 400

His Leu Gln Pro Pro Ser Tyr Gly Pro Val Leu Ser Pro Met Asn Lys
                405                 410                 415

Val His Ile His
                420
```

P40 PROTEIN ACTS AS AN ONCOGENE

This application is a divisional of prior U.S. patent application Ser. No. 09/277,196 filed Mar. 26, 1999, which claims the benefit of provisional application Ser. No. 60/079,736 filed Mar. 27, 1998, the disclosure of which is expressly incorporated herein.

The U.S. government retains certain rights in the invention due to its support via grant no. CA588401 from the National Cancer Institute.

TECHNICAL FIELD OF THE INVENTION

This invention is related to the field of cancer diagnostics and therapeutics.

BACKGROUND OF THE INVENTION p53 is the most commonly inactivated gene in human cancer and loss of critical p53 pathways are central to tumorigenesis[1,2]. The p53 protein binds specific DNA sequences and transcriptionally activates responsive genes. p53 gene mutations that occur in human cancer produce abnormal p53 proteins that are unable to bind DNA and promote the transcription and modulation of its target genes[3]. Furthermore, mutant p53 protein can act in a dominant negative manner by disturbing the function of wild type p53 protein and its ability to regulate cell proliferation[4,5]. p53 mutant protein also heterodimerizes with wild type p53 and results in a conformational change of the protein that no longer binds to p53 regulating cis-elements[6,7].

There is a continuing need in the art for a more complete understanding of the components of the pathways in which p53 acts. Moreover, there is a continuing need for improved diagnostic and therapeutic methods for treating cancers.

SUMMARY OF THE INVENTION

It is an object of the present invention to provide an isolated and purified protein useful for diagnosis and classification of cancers.

It is another object of the present invention to provide a fusion protein useful for raising antibodies and drug screening.

It is an object of the present invention to provide a preparation of antibodies useful for therapeutic intervention in cancer.

Another object of the invention is to provide a cDNA molecule, a subgenomic polynucleotide, and a nucleic acid construct which encode a protein useful for diagnosis and classification of cancers.

Another object of the invention is to provide methods of diagnosing and classifying neoplastic tissues of humans.

Another object of the invention is to provide methods of screening test compounds useful for treating cancers.

Another object of the invention is to provide a cell useful for screening test compounds useful for treating cancers.

It is yet another object of the invention to provide a method for visualizing a human chromosomal arm 3q.

It is still another object of the invention to provide therapeutic compositions and methods for treating neoplasia.

These and other objects of the invention are achieved by one or more of the following embodiments. In one embodiment an isolated and purified p40 protein is provided. It has an amino acid sequence which is at least 99% identical to SEQ ID NO:2. Percent identity is determined using a Smith-Waterman homology search algorithm using an affine gap search with a gap open penalty of 12 and a gap extension penalty of 1.

According to another embodiment of the invention a p40 fusion protein is provided which comprises a first protein segment and a second protein segment fused together by means of a peptide bond. The first protein segment consists of a p40 protein as shown in SEQ ID NO:2.

According to yet another embodiment of the invention a preparation of antibodies is provided. The antibodies specifically bind to a p40 protein having an amino acid sequence as shown in SEQ ID NO:2. The antibodies do not bind to p53 as shown in SEQ ID NO: 4.

In still another embodiment of the invention a cDNA molecule is provided which encodes a p40 protein having an amino acid sequence which is at least 99% identical to SEQ ID NO:2. Another aspect of the invention is a cDNA molecule which is at least 99% identical to the nucleotide sequence shown in SEQ ID NO:1. In still another aspect of the invention a nucleic acid construct is provided. The construct comprises: a promoter and a polynucleotide segment encoding a p40 protein as shown in SEQ ID NO:2. The polynucleotide segment is located downstream from the promoter. Transcription of the polynucleotide segment initiates at the promoter and the promoter is not the endogenous p40 promoter. Also provided is a host cell which comprises such a nucleic acid construct.

According to another embodiment of the invention a method is provided for diagnosing and classifying a neoplastic tissue of a human. Amplification of a p40 gene is detected in a tissue suspected of being neoplastic. The p40 gene has the coding sequence shown in SEQ ID NO:1. Amplification indicates neoplasia of the tissue.

Also provided is another method of identifying or classifying a neoplastic tissue of a human. Expression of a first p40 gene in a first tissue of a human suspected of being neoplastic is compared with expression of a second p40 gene in a second tissue of the human which is normal. Increased expression of the first p40 gene relative to the second p40 gene identifies the first tissue as being neoplastic and having a p40 amplification.

According to another aspect of the invention a method is provided of screening test compounds for the ability to modulate the binding of a p40 protein to a p53 protein. A test compound is contacted with a first protein comprising a p53 protein as shown in SEQ ID NO:4 and a second protein comprising a p40 protein as shown in SEQ ID NO:2. The first and second proteins bind to each other in the absence of the test compound. The amount of the first protein which is bound or unbound to the second protein or the amount of the second protein which is bound or unbound to the first protein in the presence of the test compound is determined. A test compound which modulates the amount of bound first or second protein or which modulates the amount of unbound first or second protein is a potential drug for treating cancer.

Another aspect of the invention is a method of screening test compounds for the ability to modulate the binding of a p53 protein to a p40 protein. A cell is contacted with a test compound. The cell comprises (i) a first fusion protein comprising a p40 protein as shown in SEQ ID NO:2 and either a DNA binding domain or a transcriptional activating domain; (ii) a second fusion protein comprising a p53 protein as shown in SEQ ID NO:4 and either a DNA binding domain or a transcriptional activating domain; and (iii) a reporter gene comprising a DNA sequence to which the DNA binding domain specifically binds. If the first fusion protein comprises a DNA binding domain, then the second fusion protein comprises a transcriptional activating domain, and if the first fusion protein comprises a transcriptional activating domain, then the second fusion protein comprises a DNA binding domain. The interaction of the first and second fusion proteins reconstitutes a sequence-specific transcription activating factor. The expression of the reporter gene is measured. A test compound which modulates the expression of the reporter gene is a potential anti-cancer drug.

Also provided by the present invention is a cell which comprises three recombinant DNA constructs: a first construct encodes a first polypeptide fused to a sequence-specific DNA-binding domain; a second construct encodes a second polypeptide fused to a transcriptional activation domain; and a third construct comprises a reporter gene downstream from a DNA element which is recognized by the sequence-specific DNA-binding domain. Either the first polypeptide comprises a p40 protein as shown in SEQ ID NO:2 and the second polypeptide comprises a p53 protein as shown in SEQ ID NO:4, or the first polypeptide comprises a p53 protein as shown in SEQ ID NO:4 and the second polypeptide comprises a p40 protein as shown in SEQ ID NO:2.

Another embodiment provided by the present invention is a method of visualizing a human chromosomal arm 3q. A preparation of metaphase human chromosomes is contacted with a nucleotide probe comprising at least 12 contiguous nucleotides selected from the nucleotide sequence shown in SEQ ID NO:1. A chromosome which specifically hybridizes to the nucleotide probe is detected and identified as a human chromosomal arm 3q.

According to another aspect of the invention a therapeutic composition is provided for treating neoplasia. The composition comprises a therapeutically effective amount of an antisense p40 polynucleotide and a pharmaceutically acceptable carrier.

According to another aspect of the invention a therapeutic composition is provided for treating neoplasia. The therapeutic composition comprises a therapeutically effective amount of an antibody which specifically binds to a human p40 protein and a pharmaceutically acceptable carrier.

Yet another aspect of the invention is a method of treating neoplasia. A therapeutically effective amount of a therapeutic p40 composition is administered to a patient with neoplasia, whereby the patient's neoplasia is reduced.

The present invention thus provides the art with an important new drug target which is important in the process of cancer development and progression. The target can be used diagnostically and therapeutically as well as in the screening and testing for new pharmacologic agents.

BRIEF DESCRIPTION OF THE DRAWINGS

The patent or application file contains at least one drawing executed in color. Copies of this patent or patent application publication with color drawings will be provided by the Office upon request and payment of the necessary fee.

FIG. 1 Detection of p40 expression by Northern analysis.

FIG. 2 Detection of p40 gene amplification by FISH analysis.

FIG. 6a shows a comparison of p40 to other p53 homologues. The highlighted segments are the transcriptional activation domain, the DNA binding domain, and the oligomerization domain.

FIG. 7 shows in vitro binding pull-down analysis of p40/p53 complexes. FIG. 7a shows immunoblotting of a pure GST-p53 fusion protein (10 ng) with a monoclonal antibody to p53 (BP53-12, raised against amino terminal residues 20-25, dilution 1:1000) and immunoblotting of a pure GST-midkine (20 ng) with a polyclonal antibody to midkine (M-18, raised against carboxyl terminal residues 122-140, dilution 1:1000). FIG. 7b shows cell-free translation of pCR2.1-p40 (20% input, lane 1); pull-down assay of labeled p40 protein with GST-p53 protein (100 ng) followed by precipitation with glutathione-agarose beads (lane 2); pull-down assays of the labeled p40 protein with GST-midkine (100 ng) followed by precipitation with glutathione-agarose beads (lane 4). Labeled precipitates were resolved by denaturing gel electrophoresis and dried gels were autoradiographed. Immunoblots were visualized with secondary antibodies coupled to horseradish peroxidase followed by enhanced chemiluminescence.

FIG. 8a. Saos-2 cells were infected with empty adenovirus (MOI=1, lane 1) or with P40 adenovirus (MOI=1, lane 2) for 1 h. FIG. 8b. Cell lysates were incubated with glutathione-agarose beads (lane 1) or with a pure GST-midkine (lane 2) or with a pure GST-p53 (lane 3) for 2 h at 4° C. Mixes were precipitated with 50 µl (1:1) glutathione-agarose beads and washed. Bound proteins were eluted with 10 mM reduced glutathione. Proteins were resolved by SDS-PAGE and visualized with a polyclonal antibody to p40 protein. For immunoprecipitation, cell lysates were precleared with a pre-immune rabbit serum (10 µg/500 µl) followed by a precipitation with goat anti-rabbit immunoglobulin-coupled agarose beads. Supernatants (Ad-p40, lane 4, Ad4, lane 5) were incubated with a polyclonal antibody to p40 (5 µg) for 16 h at 4° C. followed by precipitation with goat anti-rabbit immunoglobulin-coupled agarose beads for 1 h at room temperature, and analyzed by immunoblotting with a monoclonal antibody to p53 (amino terminal).

DETAILED DESCRIPTION

Figure 1A:
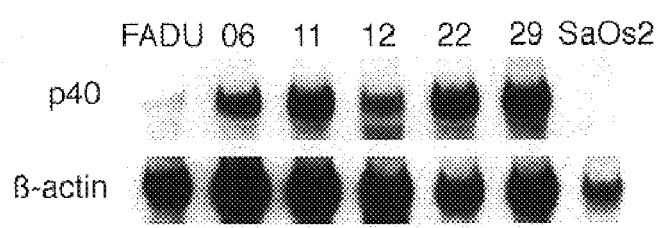
FIG. 1a, p40 transcripts in head and neck squamous cell carcinoma (HNSCC) cell lines and a sarcoma cell line, SaOs2. p40 expression is observed in all HNSCC cell lines in contrast to a lack of p40 expression in the SaOs2 cell line. A human β-actin probe was used as an internal control.
Figure 1B:
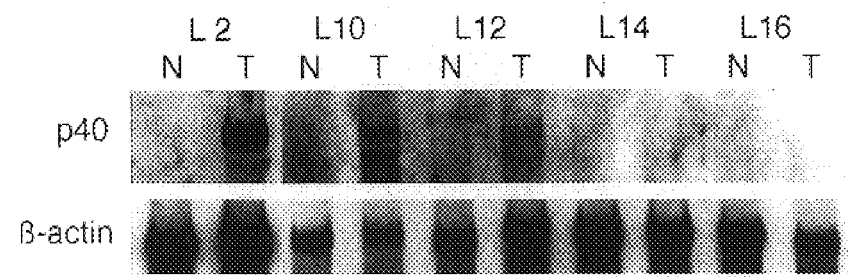
FIG. 1b, Ten μg of total RNA extracted from tumor (T) and normal (N) tissues of 5 different patients with primary lung cancers were hybridized with a $^{32}$P-labeled probe for p40 and β-actin. p40 expression varying intensity is observed in tumor RNA of cases L2, L10, L12, but is absent in all normal tissue controls.

We have isolated a new human p53 homologue, p40, and localized the gene to the distal long arm of chromosome 3[8]. The DNA binding domain and the oligomerization domain of p40 display strong conservation of amino acid residues with p53, raising the possibility that human p40 may also bind key p53 DNA binding sites in the human genome and/or interact with p53. Concurrently, an alternative p40 transcript termed p51, was cloned and shown to suppress colony formation in cell lines and to transcriptionally activate p21 in a fashion similar to the p53 tumor suppressor gene[9]. Subsequently, another group of splice variants (p63) were also described[10]. A transcript that lacked the N-terminal transactivation domain of p53 (ΔNp63) was found to act in a dominant negative fashion and to be able to suppress p53 transactivation. In contrast to these other variants, we found no evidence of a tumor suppressor function for p40. Instead, we observed p40 gene overexpression in head and neck cancer cell lines and primary lung cancers associated with a low level increase of p40 copy number. In transformation assays, Rat 1a cells with p40 expression developed larger colonies in soft agar and bigger tumors in nude mice compared to cells with an empty vector. Interestingly, binding to p53 was identified through a yeast two-hybrid system in which p40 was used as the bait. As shown previously for ΔNp63, coexpression of p40 and p53 led to a reduction of p53 transcriptional activity. Our data suggest that p40 complexes with p53 and diminishes its transcriptional activity, supporting the notion that p40 may play an oncogenic role in certain cancers.

The p40 gene maps to human chromosomal arm 3q, a region known for aberrations including deletions and amplifications in human cancers, such as bladder cancer. Amplifications of this region of chromosomal arm 3q have been observed in squamous cell carcinomas. Such carcinomas occur in head, neck, cervix, skin and lung.

Despite the initial enthusiasm surrounding the cloning of a family of p53 homologues, there has been little evidence to date as to the role of these genes in the development of human cancers. Abnormal expression of p73 has been seen in certain cancers but has been disputed by others[11,12]. Although other splice variants with a TA domain have been shown to be growth suppressive[9], our results do not support a tumor suppressor role for p40 in head and neck and lung cancers.

Conversely, our work provides tantalizing evidence that p40 may have an oncogenic role in human cancer based on the following observations: 1) the p40 gene is amplified in primary lung cancers and HNSCC cell lines by FISH analysis; 2) chromosomal amplification is associated with increased expression of RNA by Northern analysis; 3) increased gene expression is associated with increased protein accumulation by immunohistochemistry in squamous cell cancer; 4) increased p40 expression in Rat 1a cells leads to a transformed phenotype; and 5) p40 interacts with p53 and suppresses its transactivation activity on target genes.

Our data for low level p40 amplification are consistent with recent reports indicating the presence of amplification of chromosomal arm 3q in squamous cell lung carcinoma. Comparative genomic hybridization (CGH) studies indicate that squamous cell lung carcinoma commonly displays overrepresentation of the distal arm of Chromosomal arm 3q [13]. In one study, two candidate genes, BCHE and SLC2A2, were identified as possible oncogenes due to overexpression in 40% of squamous cell lung carcinomas[4]. We have demonstrated consistent p40 overexpression at the RNA and protein level in those squamous cell carcinomas with an increase in p40 copy number. This combined evidence strongly suggests a role for p40 overexpression in the progression of these cancers.

Further support for the role of p40 as an oncogene comes from our functional assays. P40 overexpression in Rat 1a cells led to a significant increase in the number and size of colonies in soft agar consistent with previous results in bonafide oncogenes[15,16]. The ability of these overexpressing cells to form larger tumors in nude mice supports the notion that p40 overexpression provides a growth advantage to tumor cells in vivo.

The physical interaction of p53 and p40 based on the yeast two-hybrid system and immunoprecipitation studies suggest an intimate association between the two members of the p53 family. Of all possible protein targets in an unbiased test, p53 was the most common clone identified with p40 as the bait. p53 protein homodimerizes and forms a tetramer before binding to DNA and transactivating downstream targets[17]. The cloning of new p53 homologues now suggests a more complex pathway for p53 action on downstream genes. It is quite plausible that p40, and perhaps other members of the p53 family of genes, may bind as heterodimers in different complexes. Depending on the individual components of these heterodimers, the protein complexes might be activating for certain downstream genes or, as suggested by co-transfection studies here and previously, might lead to a decrease in p53 transactivation. One recent study demonstrated no evidence of interaction between all p73 splice variants and p53 suggesting that the interaction between p40 and p53 described here may be more unique[18]. We still do not know the exact interaction motif between the 2 proteins and whether p40 or p53 is the critical gene that is regulated by this interaction. Further co-immunoprecipitation studies will add further light to the nature of the interaction between p40 and p53.

As noted above, p73 and some splice variants of p40 contain a putative transactivating domain capable of inducing apoptosis and tumor suppression, but there has been little evidence of inactivating point mutations or other evidence of gene inactivation in human tumors[9,10,19,20]. It appears that ΔNp63 and p40, lacking the acidic N-terminal domain, can act in a dominant negative fashion to diminish transactivation by p53. For p73, it was recently shown that different splice variants may have quite distinct effects on various p53 cis-elements[21]. Similar studies should shed further light on the specificity of p40 splice variants on target p53 promoters and their activity in the presence of p53.

Finally, our data raise a question as to why squamous cell tumors with p53 mutations appear to be associated with an increase in p40 expression. At first glance, this intriguing association suggests that p40 and p53 may be targeting different parallel pathways in tumorigenesis. However, the binding of p40 and p53 demonstrated by the yeast two-hybrid system suggests convergence of these two proteins in an oncogenic pathway. It is possible that p40 expression diminishes p53 activity providing some growth advantage to the cell followed by the eventual emergence of a p53 mutation and complete abrogation of p53 function. On the other hand, one could hypothesize that p53 mutation occurs first and that mutant p53 protein does not bind to p40 leading to an accumulation of p40 and possible promotion of its oncogenic function. As shown previously, p53 mutation can lead to an increase in genomic plasticity associated with polysomy and gene specific amplification[22,23]. This might explain the association between p53 mutation and low level chromosomal arm 3q amplification in human tumors.

The evidence presented here supports the notion that p40 amplification and overexpression plays a role in the development of squamous cell carcinoma of the upper aerodigestive tract.

Human p40 mRNA comprises a 5 kb transcript. Northern blots of human polyA+ RNA probed with a p40 nucleotide probe demonstrate that the 5 kb transcript is expressed, inter alia, in prostate.

Human p40 polypeptides preferably comprise at least 6, 10, 12, 14, 15, 18, 20, 25, 30, or 35 contiguous amino acids of the amino acid sequence shown in SEQ ID NO:2. Human p40 proteins and polypeptides can be isolated and purified from human cells such as prostate cells.

Human p40 protein has the amino acid sequence shown in SEQ ID NO:2. Any naturally occurring variants of this sequence which may occur in human tissues and which have, for example, oncogenic or proliferation-inducing activity, are within the scope of this invention. Nonnaturally occurring p40 variants which differ by as much as 1% are also encompassed.

Preferably the amino acid changes in p40 variants or derivatives are conservative amino acid changes, i.e., substitutions of similarly charged or uncharged amino acids. A conservative amino acid change involves substitution of one of a family of amino acids which are related in their side chains. Naturally occurring amino acids are generally divided into four families: acidic (aspartate, glutamate), basic (lysine, arginine, histidine), non-polar (alanine, valine, leucine, isoleucine, proline, phenylalanine, methionine, tryptophan), and uncharged polar (glycine, asparagine, glutamine, cystine, serine, threonine, tyrosine) amino acids. Phenylalanine, tryptophan, and tyrosine are sometimes classified jointly as aromatic amino acids. It is reasonable to expect that an isolated replacement of a leucine with an isoleucine or valine, an aspartate with a glutamate, a threonine with a serine, or a similar replacement of an amino acid with a structurally related amino acid will not have a major effect on the binding properties of the resulting molecule, especially if the replacement does not involve an amino acid at a binding site involved in an interaction of p40 protein. Whether an amino acid change results in a functional p40 protein or polypeptide can readily be determined by assaying the properties of the protein or polypeptide, as described below. Variants of p40 proteins have substantially the same biological activities, that is, for example, p53-binding activities which are of the same type as a p40 protein having the amino acid sequence shown in SEQ ID NO:2, although the activities may differ in degree.

p40 proteins or polypeptides can be purified by any method known in the art. These methods include, but are not limited to, size exclusion chromatography, ammonium sulfate fractionation, ion exchange chromatography, affinity chromatography, crystallization, electrofocusing, immunoprecipitation, immunoaffinity chromatography, and preparative gel electrophoresis. The skilled artisan can readily select methods which will result in a preparation of p40 protein or polypeptide which is substantially free from other proteins and from carbohydrates, lipids, or subcellular organelles. A preparation of isolated and purified p40 protein is at least 80% pure; preferably, the preparations are 90%, 95%, or 99% pure. Purity of the preparations may be assessed by any means known in the art, such as SDS-polyacrylamide gel electrophoresis.

p40 proteins and polypeptides can also be produced by recombinant DNA methods or by synthetic chemical methods. For production of recombinant p40 proteins or polypeptides, coding sequences selected from the nucleotide sequence shown in SEQ ID NO:1 can be expressed in known prokaryotic or eukaryotic expression systems. Bacterial, yeast, insect, or mammalian expression systems can be used, as is known in the art. Alternatively, synthetic chemical methods, such as solid phase peptide synthesis, can be used to synthesize p40 protein or polypeptides.

p40 fusion proteins are useful for generating antibodies against p40 amino acid sequences and for use in various assay systems. For example, p40 fusion proteins can be used to identify proteins which interact with p40 protein and influence its function. Physical methods, such as protein affinity chromatography, or library-based assays for protein-protein interactions, such as the yeast two-hybrid or phage display systems, can be used for this purpose. Such methods are well known in the art and can be used, inter alia, as drug screens.

A p40 fusion protein comprises two protein segments fused together by means of a peptide bond. The first protein segment comprises at least 8, 10, 12, 15, or 20 contiguous amino acids of a p40 protein. The amino acids can be selected from the amino acid sequence shown in SEQ ID NO:2 or from a naturally or nonnaturally occurring biologically active variant of that sequence, such as those described above. The first protein segment can also be a full-length p40 protein. The second protein segment can be a full-length protein or a protein fragment or polypeptide. The fusion protein can be labeled with a detectable marker, as is known in the art, such as a radioactive, fluorescent, chemiluminescent, or biotinylated marker. The second protein segment can be an enzyme which will generate a detectable product, such as β-galactosidase or other enzymes which are known in the art. The second protein can have any useful property, such as affinity to an analytic reagent or immunogenicity. The first protein segment may be N-terminal or C-terminal to the second protein segment, as is convenient.

Techniques for making fusion proteins, either recombinantly or by covalently linking two protein segments, are also well known. Recombinant DNA methods can be used to construct p40 fusion proteins, for example, by making a DNA construct which comprises coding sequences selected from SEQ ID NO:1 in proper reading frame with nucleotides encoding the second protein segment and expressing the DNA construct in a host cell, as described below.

Figure 6B:
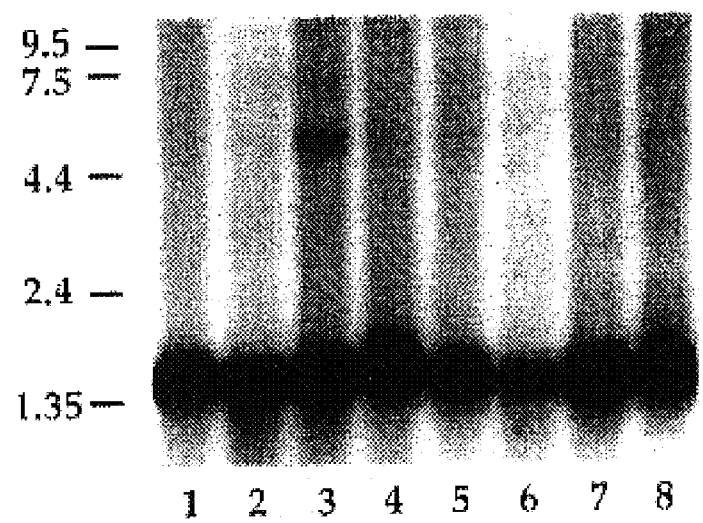
FIG. 6b shows a multiple tissue northern blot probed with a cloned 180 bp product of p40 and GAPDH as a control. Lanes: 1, spleen; 2, thymus; 3, prostate; 4, testis, 5, ovary; 6, small intestine; 7, colon; 8, peripheral blood leukocytes.
Figure 6C:
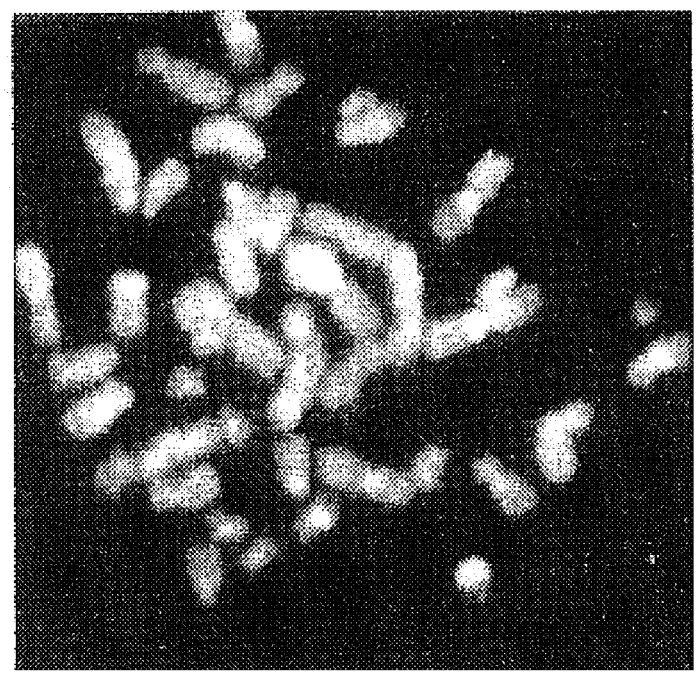
FIG. 6c shows a FISH analysis of a BAC8836 probe (Genome Systems) on a metaphase nucleus of a normal human lymphocyte with the centromeric probe of chromosome 3 hybridized simultaneously. Signals from the BAC probe were seen on the telomeric end of the long arm of chromosome 3.
Figure 9:
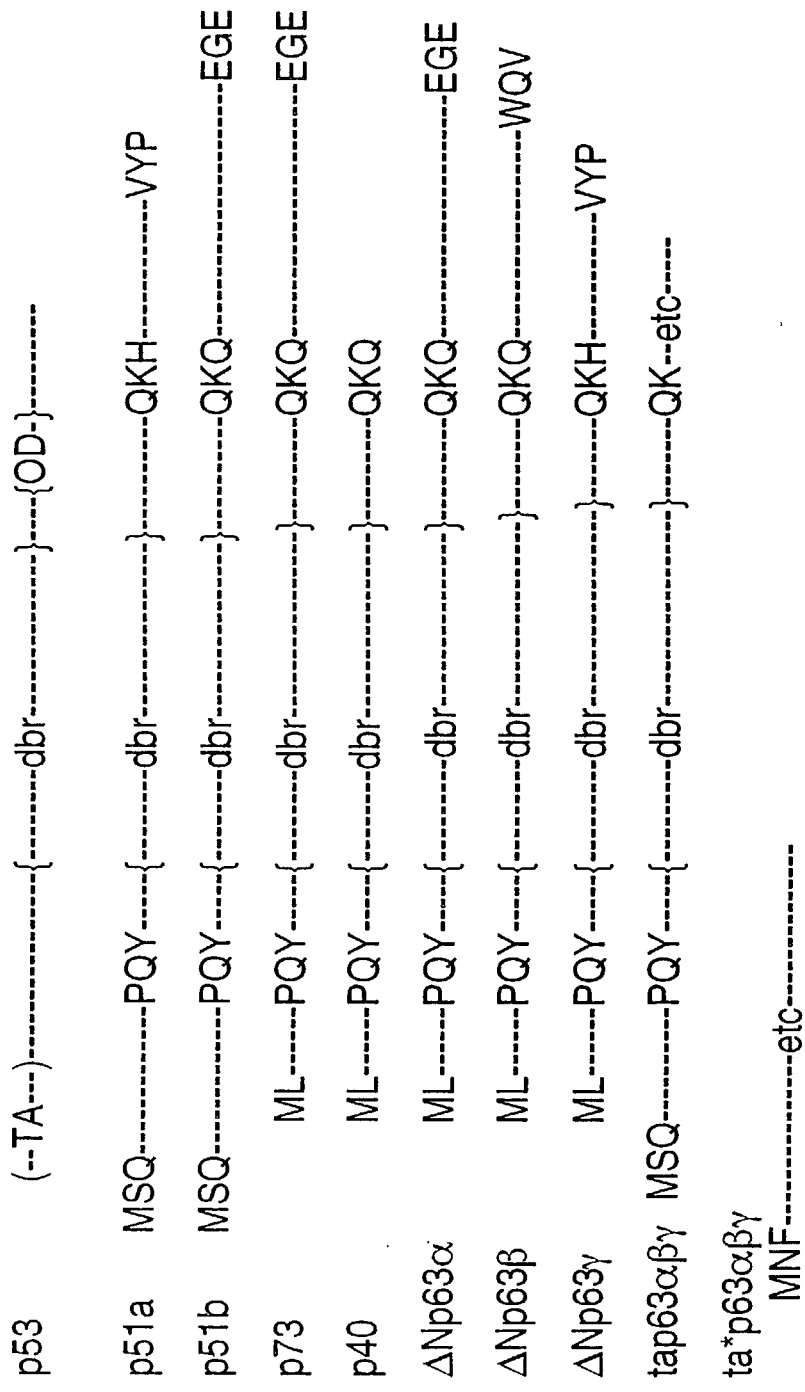
FIG. 9 shows a schematic comparison of members of the p53 family including p40 splice variants.

Isolated and purified p40 proteins, polypeptides, or fusion proteins can be used as immunogens, to obtain a preparation of antibodies which specifically bind to a p40 protein. The antibodies can be used to detect p40 proteins in human tissue and fractions thereof. The antibodies can also be used to detect the presence of amplification of the p40 gene which results in overexpression of the p40 protein or in expression.

p40-specific antibodies specifically bind to a p40 polypeptide. p40-specific antibodies bind to p40 and have a measurably higher binding affinity for a p40 polypeptide than for non-p40 polypeptides, particularly p53. Higher affinity by a factor of 5, or 10 is preferred, more preferably by a factor of 100. The antibodies may be polyclonal or monoclonal. They are preferably raised against portions of the protein which differ significantly from p53 and its other homologues. See FIG. 6 which compares the amino acid seqeunce of p40 to other p53 homologues.

Preparations of polyclonal and monoclonal p40 antibodies can be made using standard methods known in the art. The antibodies specifically bind to epitopes present in p40 proteins having the amino acid sequence shown in SEQ ID NO:2 or in naturally or non-naturally occurring variants of that sequence. Preferably, the p40 epitopes are not present in other human proteins. Typically, at least 6, 8, 10, or 12 contiguous amino acids are required to form an epitope. However, epitopes which involve non-contiguous amino acids may require more, e.g., at least 15, 25, or 50 amino acids. Antibodies which specifically bind to p40 proteins provide a detection signal at least 5-, 10-, or 20-fold higher than a detection signal provided with other proteins when used in Western blots or other immunochemical assays. Preferably, antibodies which specifically bind p40 proteins do not detect other proteins in immunochemical assays and can immunoprecipitate p40 proteins from solution.

Human p40 antibodies can be purified by methods well known in the art. Preferably, the antibodies are affinity purified, by passing antiserum over a column to which a p40 protein, polypeptide, or fusion protein is bound. The bound antibodies can then be eluted from the column, for example, using a buffer with a high salt concentration.

Purified and isolated p40 subgenomic polynucleotides can be used, inter alia, as primers to obtain additional copies of the polynucleotides, to express human p40 mRNA, protein, polypeptides, or fusion proteins, and as probes for identifying p40 coding sequences. The probes can also be used to identify the long arm of a human chromosome 3, as described below.

Purified and isolated p40 subgenomic polynucleotides of the invention comprise at least 11, 13, 15, 18, 20, 25, or 30 contiguous nucleotides selected from SEQ ID NO:1. Subgenomic p40 polynucleotides according to the invention contain less than a whole chromosome. Preferably, the polynucleotides are intron-free, i.e., cDNA.

Subgenomic p40 polynucleotides can be isolated and purified free from other nucleotide sequences using standard nucleic acid purification techniques. For example, restriction enzymes and probes can be used to isolate polynucleotide fragments which comprise p40 coding sequences. Isolated polynucleotides are in preparations which are free or at least 90% free of other molecules.

DNA fragments derived from a p40-encoding DNA sequence are also included herein. A DNA fragment derived from a p40 coding sequence has the same or substantially the same basepair sequence as a region of the coding sequence of the entire p40 molecule. Preferably the DNA fragment has at least 99% identity with p40.

Complementary DNA encoding p40 proteins can be made using reverse transcriptase, with p40 mRNA as a template. The polymerase chain reaction (PCR) can be used to obtain p40 polynucleotides, using either human genomic DNA or cDNA as a template. Alternatively, synthetic chemistry techniques can be used to synthesize polynucleotide molecules of the invention. The degeneracy of the genetic code allows alternate nucleotide sequences to be synthesized which will encode a p40 protein having the amino acid sequence shown in SEQ ID NO:2. All such nucleotide sequences are within the scope of the present invention.

A p40 subgenomic polynucleotide of the present invention can be used in an expression construct, to express all or a portion of a p40 protein in a host cell. The host cell comprising the expression construct can be prokaryotic or eukaryotic. A variety of host cells for use in bacterial, yeast, insect, and human expression systems are available and can be used to express the expression construct. The expression constructs can be introduced into the host cells using any technique known in the art. These techniques include transferrin-polycation-mediated DNA transfer, transfection with naked or encapsulated nucleic acids, liposome-mediated cellular fusion, intracellular transportation of DNA-coated latex beads, protoplast fusion, viral infection, electroporation, and calcium phosphate-mediated transfection.

The expression construct comprises a promoter which is not the p40 endogenous promoter and which is functional in the particular host cell selected. The skilled artisan can readily select an appropriate promoter from the large number of cell type-specific promoters known and used in the art. The expression construct can also contain a transcription terminator which is functional in the host cell. The expression construct comprises a polynucleotide segment which encodes all or a portion of a p40 protein. The polynucleotide segment is located downstream from the promoter. Transcription of the polynucleotide segment initiates at the promoter. The expression construct can be linear or circular and can contain sequences, if desired, for autonomous replication.

The p40 gene maps to human chromosome region 3q. Thus, the subgenomic polynucleotides of the invention can be used to identify this chromosome region in metaphase spreads of human chromosomes. Preparations of human metaphase chromosomes can be prepared using standard cytogenetic techniques from human primary tissues or cell lines. Nucleotide probes comprising at least 12 contiguous nucleotides selected from the nucleotide sequence shown in SEQ ID NO:1 are used to identify the human chromosome. The nucleotide probes can be labeled, for example, with a radioactive, fluorescent, biotinylated, or chemiluminescent label, and detected by well known methods appropriate for the particular label selected. Protocols for hybridizing nucleotide probes to preparations of metaphase chromosomes are well known in the art. A nucleotide probe will hybridize specifically to nucleotide sequences in the chromosome preparations which are complementary to the nucleotide sequence of the probe. A probe which hybridizes specifically to the p40 gene does not hybridize to nucleotide sequences present in other human genes. A probe which hybridizes specifically to a p40 gene provides a detection signal at least 5-, 10-, or 20-fold higher than the background hybridization provided with non-p40 coding sequences.

A human chromosome which specifically hybridizes to a p40 nucleotide probe is identified as a human chromosome 3. In particular, the nucleotide probe identifies the long arm of human chromosome 3. Quantitation of the hybridization can be used to detect amplification of the p40 gene. Typically the amplification is less than 10-fold, and more typically it is less than 5-fold.

The present invention also provides a method to identify and classify neoplastic tissue in a human. The expression of a p40 gene can be compared between a first tissue which is suspected of being neoplastic and a second tissue of the human which is normal. The normal tissue can be any tissue of the human, especially those which express the p40 gene, including, but not limited to, prostate. The tissue suspected of being neoplastic can be derived from a different tissue type of the human, but preferably it is derived from the same tissue type. A difference in abundance of the p40 gene, mRNA, or protein in the two tissues which are compared indicates a somatic mutation in the p40 gene in the tissue of the human which was suspected of being neoplastic.

Alternatively, p40 mRNA in the two tissues can be compared. PolyA+ RNA can be isolated from the two tissues as is known in the art. For example, one of skill in the art can readily determine differences in the amount of p40 mRNA transcripts between the two tissues that are compared, using Northern blots and nucleotide probes selected from the nucleotide sequence shown in SEQ ID NO:1. Increased expression of p40 mRNA in a tissue sample suspected of being neoplastic compared with the expression of p40 mRNA in a normal tissue is indicative of neoplasia.

Any method for analyzing proteins can be used to compare two p40 proteins from matched samples. For example, antibodies of the present invention can be used to detect p40 proteins in Western blots of protein extracts from the two tissues to detect changes in expression levels. A higher p40 protein expression level in a tissue suspected of being neoplastic compared with the p40 protein expression level in a normal tissue is indicative of neoplasia.

Similarly, comparison of p40 gene sequences between a tissue of a human which is suspected of being neoplastic and a normal tissue of a human can be used to diagnose or classify cancers in the human. Observation of amplification of p40 in the neoplastic tissue over time can be used to monitor the progression of the neoplasia in that tissue or to predict or monitor the response of the neoplastic tissue to various therapeutic regimens.

According to another aspect of the invention, test compounds can be screened for utility as anti-cancer agents by the ability to suppress the expression or function of human p40 protein. Potential drugs can be contacted with cells and the expression of p40 mRNA or protein monitored. This can be accomplished by well known techniques in the art, such as Northern blots, immunoprecipitation, immunoblots, etc. Any technique which utilizes a p40 nucleic acid probe or an antibody specific for p40 protein can be used. Other techniques, such as quantitative reverse PCR can also be employed.

In addition, in vitro techniques can be employed for testing the ability of candidate drugs to modulate p40 binding to p53. Such assays are well within the skill of the art, once provided with the full sequences of the p40 and p53 genes and proteins. In addition, a yeast two-hybrid system can be used wherein one of the partners is p40 and one of the partners is p53. A cell which contains both of these partners can be contacted with test compounds and the augmentation or diminution of transactivation of the reporter gene can be monitored.

Modulators of p53-p40 binding can be, for example, polypeptides, small peptides, peptoids, or other peptide analogs or other chemical inhibitors. Some of these inhibitors, such as related peptides or fusion proteins, can be developed rationally on the basis of knowledge of the sequences of p53 and p40 which are disclosed herein. Alternatively, a random array of compounds can be screened for the ability to affect in a p53-p40 binding assay.

The test compounds can be pharmacologic agents already known in the art or can be compounds previously unknown to have any pharmacological activity. The compounds can be naturally occurring or designed in the laboratory. They can be isolated from microorganisms, animals, or plants, and can be produced recombinantly, or synthesized by chemical methods known in the art.

A test compound can be contacted with a mixture of a p40 protein and a p53 protein. These molecules can be produced recombinantly or can be synthesized using standard chemical methods. The proteins can be pre-bound prior to the step of contacting the test compound. Alternatively, the test compound can contact one of the proteins before the second protein is added.

The proteins can be in solution or one protein can be bound to a solid support. Alternatively, the proteins can be co-expressed in a cell. The proteins can be unlabeled or labeled, for example, with a radioactive, fluorescent, or other detectable marker. They can be fusion proteins comprising p53 or p40 fused to another protein with or without a detectable enzymatic activity.

In one embodiment, the amount of at least one of the two proteins that is bound or unbound in the presence of the test compound is then measured. A number of methods can be used to measure the amount of bound or unbound protein. For example, the relative concentration of proteins bound to unbound can be detected by examining the apparent molecular masses of the molecules by size exclusion chromatography or by polyacrylamide gel electrophoresis under non-reducing conditions. If the proteins are in a cell, the transactivation by p53 of down-stream genes can be monitored as a means of measuring the amount bound. Other methods of measuring binding or dissociation of the proteins will readily occur to those of ordinary skill in the art and can be used. A test compound which modulates the quantity of one protein bound to a second protein is identified as a candidate therapeutic agent. While applicants are not bound by any particular theory of operation, enhanced binding of p40 could prevent its actions as an oncogene. Conversely, diminished binding of p53 could augment its actions as a tumor suppressor. According to the present invention a method is also provided of using the yeast two-hybrid technique to screen for test compounds which modulate with p53-p40 binding. The yeast two-hybrid technique is taught in Fields & Song, Nature 340, 245-46, 1989. In a preferred embodiment, a cell is contacted with a test compound. The cell comprises two fusion proteins, which can be supplied to the cell by means of recombinant DNA constructs. The first fusion protein comprises a DNA-binding domain. The second fusion protein comprises a transcriptional activating domain. The first fusion protein also comprises either (i) p40 or (ii) a p53. If the first fusion protein comprises p53, then the second fusion protein comprises p40. If the first fusion protein comprises p40, then the second fusion protein comprises p53. The cell also comprises a reporter gene comprising a DNA sequence downstream from a DNA element to which the first fusion protein binds.

When the p40 and p53 proteins are bound together, the DNA binding domain and the transcriptional activating domain will be in close enough proximity to reconstitute a transcriptional activator capable of initiating transcription of the detectable reporter gene in the cell. The expression of the reporter gene in the presence of the test compound is then measured. A test compound that increases the expression of the reporter gene is a potential drug for increasing p53-p40 binding. A test compound that decreases the expression of the reporter gene is a potential drug for decreasing p53-p40 binding.

Many DNA binding domains and transcriptional activating domains can be used in this system, including the DNA binding domains of GAL4, LexA, and the human estrogen receptor paired with the acidic transcriptional activating domains of GAL4 or the herpes virus simplex protein VP16 (see, e.g., Hannon et al., *Genes Dev.* 7, 2378, 1993; A. S. Zervos et al., *Cell* 72, 223, 1993; A. B. Votjet et al., *Cell* 74, 205, 1993; Harper et al., *Cell* 75, 805, 1993; B. Le Douarin et al., *Nucl. Acids Res.* 23, 876, 1995). A number of plasmids known in the art can be constructed to contain the coding sequences for the fusion proteins using standard laboratory techniques for manipulating DNA (see, e.g., Example 1, below).

Suitable detectable reporter genes include the *E. coli* lacZ gene, whose expression can be measured calorimetrically (see, e.g., Fields and Song), and yeast selectable genes such as HIS3 (Harper et al.; Votjet et al.; Hannon et al.) or URA3 (Le Douarin et al.). Methods for transforming cells are also well known in the art. See, e.g., a. Hinnen et al., *Proc. Natl. Acad. Sci. U.S.A.* 75, 1929-1933, 1978. The test compound can comprise part of the cell culture medium or it may be added separately.

Antisense polynucleotides of the p40 gene can be used to interfere with expression of the p40 gene. Antisense polynucleotides are typically generated within the cell by expression from antisense constructs which contain the antisense p40 strand as the transcribed strand from a promoter. A description of vectors which can be used to introduce antisense constructs to a cell is contained in U.S. Ser. No. 08/869,309, which is expressly incorporated herein. Antisense p40 polynucleotides will bind and/or interfere with the translation of p40 mRNA.

The invention provides a therapeutic composition for inhibiting a p40 oncogene function in a cell. Inhibition of p40 expression suppresses neoplasia, dysplasia, or hyperplastic cell growth. The cell to be treated can be any cell of a human which expresses the p40 oncogene, such as a cell of the prostate, lung, skin, head, neck, and cervix. Such cells include those in neoplasias of the tissues mentioned above as well as any other neoplastic cells which express the p40 gene. The therapeutic composition can comprise the antisense strand of all or a portion of human p40 gene in a pharmaceutically acceptable carrier. The therapeutic composition can comprise an antisense construct which produceds an antisense strand RNA in a cell. The p40 antisense product can be, e.g., mRNA or DNA. Alternatively, the therapeutic composition can comprise antibodies which specifically bind to p40 proteins or polypeptides.

Pharmaceutically acceptable carriers are well known to those in the art. Such carriers include, but are not limited to, large, slowly metabolized macromolecules, such as proteins, polysaccharides, polylactic acids, polyglycolic acids, polymeric amino acids, amino acid copolymers, and inactive virus particles. Pharmaceutically acceptable salts can also be used in the composition, for example, mineral salts such as hydrochlorides, hydrobromides, phosphates, or sulfates, as well as the salts of organic acids such as acetates, proprionates, malonates, or benzoates. The composition can also contain liquids, such as water, saline, glycerol, and ethanol, as well as substances such as wetting agents, emulsifying agents, or pH buffering agents. Liposomes, such as those described in U.S. Pat. No. 5,422,120, WO 95/13796, WO 91/14445, or EP 524,968 B1, can also be used as a carrier for the therapeutic p40 composition.

Typically, the therapeutic p40 composition is prepared as an injectable, either as a liquid solution or suspension; however, solid forms suitable for solution in, or suspension in, liquid vehicles prior to injection can also be prepared. The composition can also be formulated into an enteric coated tablet or gel capsule according to known methods in the art, such as those described in U.S. Pat. No. 4,853,230, EP 225,189, AU 9,224,296, and AU 9,230,801.

Proliferative disorders, such as neoplasias, dysplasias, and hyperplasias, can be treated by administration of the therapeutic p40 composition. Neoplasias which can be treated with the therapeutic composition include, but are not limited to, melanomas, squamous cell carcinomas, and head, neck, cervix, and skin cancers. Proliferative disorders which can be treated with the therapeutic p40 composition include disorders such as anhydric hereditary ectodermal dysplasia, congenital alveolar dysplasia, epithelial dysplasia of the cervix, fibrous dysplasia of bone, and mammary dysplasia. Hyperplasias, for example, endometrial, adrenal, breast, prostate, or thyroid hyperplasias, or pseudoepitheliomatous hyperplasia of the skin can be treated with wild-type p40 therapeutic compositions. Even in disorders in which p40 overexpression is not implicated, down-regulation of p40 expression or suppression of p40 function can have therapeutic application. In these disorders, decreasing p40 expression or suppressing p40 function can help to suppress tumors. Similarly, in tumors where p40 expression is not aberrant, effecting p40 down-regulation of p40 expression or suppression of p40 activity can suppress metastases.

Administration of the therapeutic agents of the invention can include local or systemic administration, including injection, oral administration, particle gun, or catheterized administration, and topical administration. Various methods can be used to administer the therapeutic p40 composition directly to a specific site in the body. For example, a small metastatic lesion can be located and the therapeutic p40 composition injected several times in several different locations within the body of tumor. Alternatively, arteries which serve a tumor can be identified, and the therapeutic composition injected into such an artery, in order to deliver the composition directly into the tumor. A tumor which has a necrotic center can be aspirated and the composition injected directly into the now empty center of the tumor. The therapeutic p40 composition can be directly administered to the surface of the tumor, for example, by topical application of the composition. X-ray imaging can be used to assist in certain of the above delivery methods. Combination therapeutic agents, including a p40 antibody or an antisense p40 polynucleotide and other therapeutic agents, can be administered simultaneously or sequentially.

Receptor-mediated targeted delivery of therapeutic compositions containing antisense p40 subgenomic polynucleotides to specific tissues can also be used. Receptor-mediated DNA delivery techniques are described in, for example, Findeis et al. (1993), *Trends in Biotechnol.* 11, 202-05; Chiou et al. (1994), GENE THERAPEUTICS: METHODS AND APPLICATIONS OF DIRECT GENE TRANSFER (J. A. Wolff, ed.); Wu & Wu (1988), *J. Biol. Chem.* 263, 621-24; Wu et al. (1994), *J. Biol. Chem.* 269, 542-46; Zenke et al. (1990), *Proc. Natl. Acad. Sci. U.S.A.* 87, 3655-59; Wu et al. (1991), *J. Biol. Chem.* 266, 338-42.

Alternatively, a p40 therapeutic composition can be introduced into human cells ex vivo, and the cells then replaced into the human. Cells can be removed from a variety of locations including, for example, from a selected tumor or from an affected organ. In addition, the therapeutic composition can be inserted into non-tumorigenic cells, for example, dermal fibroblasts or peripheral blood leukocytes. If desired, particular fractions of cells such as a T cell subset or stem cells can also be specifically removed from the blood (see, for example, PCT WO 91/16116). The removed cells can then be contacted with a p40 therapeutic composition utilizing any of the above-described techniques, followed by the return of the cells to the human, preferably to or within the vicinity of a tumor. The above-described methods can additionally comprise the steps of depleting fibroblasts or other non-contaminating tumor cells subsequent to removing tumor cells from a human, and/or the step of inactivating the cells, for example, by irradiation.

Both the dose of the p40 composition and the means of administration can be determined based on the specific qualities of the therapeutic composition, the condition, age, and weight of the patient, the progression of the disease, and other relevant factors. If the composition contains p40 antibody, effective dosages of the composition are in the range of about 5 µg to about 50 µg/kg of patient body weight, about 50 µg to about 5 mg/kg, about 100 µg to about 500 µg/kg of patient body weight, and about 200 to about 250 µg/kg.

Therapeutic compositions containing p40 antisense subgenomic polynucleotides can be administered in a range of about 100 ng to about 200 mg of DNA for local administration in a gene therapy protocol. Concentration ranges of about 500 ng to about 50 mg, about 1 µg to about 2 mg, about 5 µg to about 500 µg, and about 20 µg to about 100 µg of DNA can also be used during a gene therapy protocol. Factors such as method of action and efficacy of transformation and expression are considerations that will effect the dosage required for ultimate efficacy of the antisense p40 subgenomic polynucleotides. Where greater expression is desired over a larger area of tissue, larger amounts of antisense p40 subgenomic polynucleotides or the same amounts readministered in a successive protocol of administrations, or several administrations to different adjacent or close tissue portions of, for example, a tumor site, may be required to effect a positive therapeutic outcome. In all cases, routine experimentation in clinical trials will determine specific ranges for optimal therapeutic effect.

The above disclosure generally describes the present invention. A more complete understanding can be obtained by reference to the following specific examples which are provided herein for purposes of illustration only, and are not intended to limit the scope of the invention.

EXAMPLE 1 p40 as a Tumor Suppressor Gene

We first examined the p40 gene sequence using cDNA from 14 primary lung cancers, and 6 head and neck squamous cell carcinoma (HNSCC) cell lines (Table 1). Two missense variants were observed. These changes involved Codon 298 (Lys to Arg) in a primary lung cancer (#7904086) and Codon 14 (Glu to Gln) in a HNSCC (#11). Although paired normal DNA was not available to confirm the somatic origin of these alterations, the conserved nature of these missense variants suggested that inactivation of p40 in these human cancers is uncommon.

Because of its structural similarity to p53, we next examined whether p40 demonstrated tumor suppressive effects using adenovirus vector constracts. SaOs2 cells that have no expression of p53 (p53−/−) and p40 (FIG. 1a) were infected with a replication incompetent adenovirus containing the p40 gene under the control of the CMV promoter and an adenovirus vecter control (multiplicity of infection (MOI)=3). Cell numbers were counted on days 1, 3, 5, and 7 after infection and cells infected with the p40 adenovirus demonstrated no difference in cell number or viability compared to the control (data not shown). In contrast, SaOs2 cells infected with a p53 adenovirus showed rapid cell death within 48 hrs of infection. Overall, these results provided little evidence of a tumor suppressor gene function for p40.

p40 Adenoviral Vector

A full length p40 cDNA was cloned from human prostate cDNA library as previously described[8]. The construct was then subcloned into the shuttle vector, pAdTrack-CMV. The resultant plasmid was linearized by digesting with the restriction endonuclease Pme I, and subsequently cotransformed into E. coli. BJ5183 cells with an adenoviral backbone plasmid, pAdEasy-1. Recombinants were selected for kanamycin resistance, and recombination was confirmed by restriction digest analysis. The linearized recombinant plasmid was then transfected into the adenovirus packaging cell line, 293, that was described in detail previously[24].

EXAMPLE 2

Overexpression and Polysomy of Chromosome 3

Figure 2A:
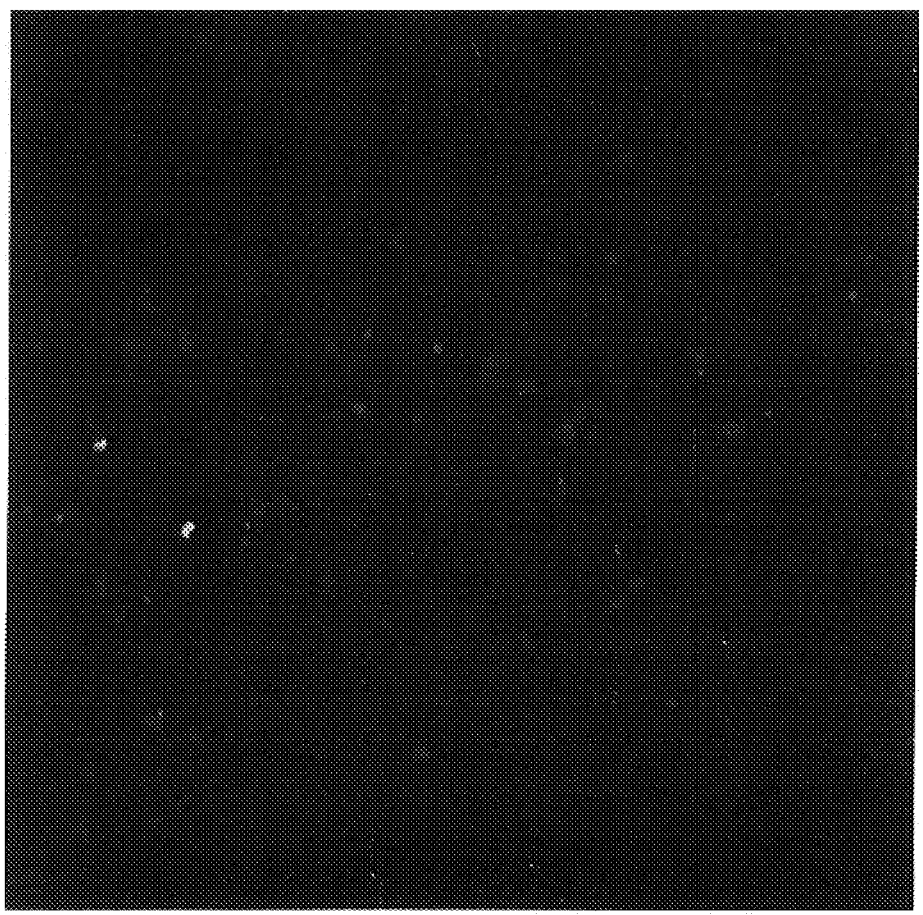
FIG. 2a, Low level p40 gene amplification (BAC probe, red) was observed on metaphase and interphase nuclei of the HNSCC cell line (FADU) compared to a chromosome 3 centromeric probe (green). FADU is known to have an abnormal chromosome 3 karyotype; der(3)t(3:8)(q21:q?). Six signals from the BAC probe were seen on the telomeric end of the long arm of chromosome 3 and on the short arm of chromosome 3 compared to 4 signals from the chromosome 3 centromeric probe. As a control, normal lymphocytes were subjected to the same FISH analysis to confirm that the p40 probe had no cross-hybridization with other chromosomal regions.
Figure 2B:
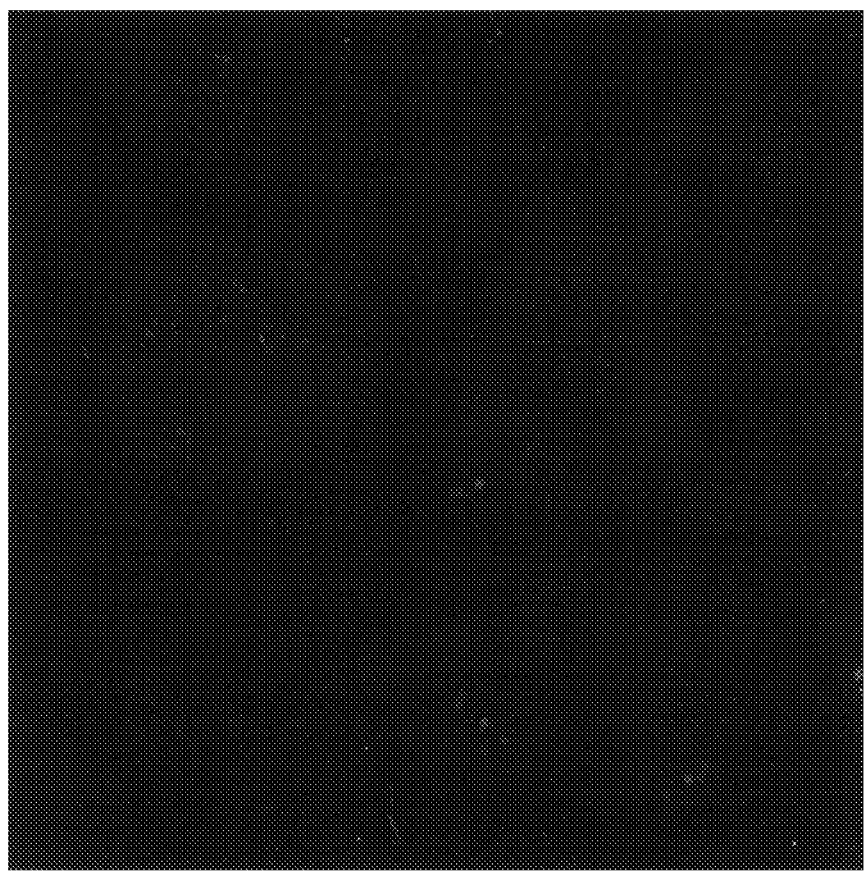
FIG. 2b, A similar FISH analysis on a primary squamous cell lung carcinoma (T21) demonstrating 2 centromeric signals (green) and 3-4 p40 signals (red) per tumor cell.

We then examined p40 gene expression in primary lung cancers and HNSCC cell lines by Northern analysis. We found that 10 of 14 primary lung cancers (71%) and all 6 HNSCC cell lines (100%) demonstrated p40 gene overexpression while normal paired lung tissue and a normal embryonic lung cell line revealed virtual absence of p40 gene expression (FIGS. 1a, b). Subsequently, we examined p40 gene amplification by fluorescent in situ hybridization (FISH) (FIG. 2). FISH analysis suggested 3 to 5 fold amplification of the p40 locus in 12 of 23 primary lung cancers (52%) and all 6 HNSCC cell lines (100%) (Table 1). In some cases, a concordant increase in chromosomal arm 3q with a centromeric probe was also observed confirming the presence of polysomy. The amplification data from FISH analysis correlated with expression data from Northern analysis in all 6 HNSCC cell lines and the squamous cell lung cancers (see below).

We then tested p40 protein expression in primary lung cancers and HNSCC cell lines using immunohistochemistry. Ten of 23 primary lung cancers (43%) and all 6 HNSCC cell lines (100%) had p40 protein overexpression (FIG. 3) (Table 1). As shown previously, p40 nuclear staining was present at the basal layer of the bronchial epithelium[10]. P40 nuclear expression was characteristic of those cancers with increased p40 protein and, interestingly, all of the positive samples were squamous cell carcinomas and all had chromosome 3 polysomy or more specific p40 amplification (Table 2). In contrast, no adenocarcinomas had p40 protein overexpression (P<0.0001, Fisher's exact test), suggesting that low level p40 amplification correlates with abundant p40 protein only in squamous cell carcinoma.

We also examined the relationship between histology and p40 gene amplification in lung cancer. All 10 squamous cell carcinomas (100%) and only 2 of 13 adenocarcinomas (15%) demonstrated polysomy and/or p40 locus amplification (p<0.0001) (Table 2). Together with our amplification and immunohistochemistry data, it appeared that true p40 amplification was characteristic of squamous cell carcinoma of the lung and head and neck.

To examine a possible relationship between p40 gene amplification and p53 status, we proceeded with sequence analysis of the p53 gene (exon 5 to 8) in the primary lung cancers. Remarkably, out of 10 primary lung cancers with p40 protein overexpression, 8 (80%) had p53 mutations (p=0.0361) (Table 2). This association suggested a possible relationship between overexpression of p40 and a tumor suppressor gene role for p53 in human cancers.

TABLE 1 p40 status in primary lung cancers and HNSCC cell lines

| | Sample Total number | sequence variants | expression (Northern) | immuno-histochemistry | increased copy |
|---|---|---|---|---|---|
| primary lung cancer | | | | | |
| total RNA | 1/14 (7%) | 10/14 (71%) | — | — | 14 |
| sections | — | — | 10/23 (43%) | 13/23 (57%) | 23 |
| HNSCC cell line | 1/6 (17%) | 6/6 (100%) | 6/6 (100%) | 6/6 (100%) | 6 |

TABLE 2 p40 and p53 status in 23 primary lung cancers*

| Sample | increased copy number (p40) | immuno-histochemistry (p40) | mutation (p53) |
|---|---|---|---|
| squamous cell carcinoma | | | |
| L10 | + | + | + |
| T1 | + | + | + |
| T3 | + | + | + |
| T13 | + | + | + |
| T14 | + | + | − |
| T17 | + | + | + |
| T20 | + | + | − |
| T21 | + | + | + |
| T22 | + | + | + |
| T23 | + | + | + |
| total | 10/10 (100%)† | 10/10 (100%)‡ | 8/10 (80%) |
| adenocarcinoma | | | |
| L2 | + | − | − |
| L4 | − | − | − |
| L6 | − | − | − |
| L12 | + | − | + |
| L14 | − | − | − |
| L16 | − | − | − |
| T24 | − | − | − |
| T25 | − | − | + |
| T26 | − | − | + |
| T29 | − | − | + |
| T31 | − | − | − |
| T34 | − | − | − |
| T35 | − | − | − |
| total | 2/13 (15%) | 0/13 (0%) | 4/13 (31%) |

*Five primary lung cancers only had total RNA available for analysis
† ‡P < 0.0001 (Fisher's exact test for squamous cell carcinoma vs. adenocarcinoma)

Mutation Analysis for the p40 and p53 Gene

The PCR amplification of tumor cDNA samples consisted of 35 cycles of 95° C. for 1 min, 55° C. for 1 min, 72° C. for 1 min. The primers used were: p40 S1 (sense), 5'-GCAGCAT-TGATCAATCTTACAG and p40 AS2 (antisense), 5'-TGAATTCACGGCTCAGCTCAT; p40 S3 (sense), 5'-CGCCATGCCTGTCTACAAAAA and p40 AS4 (antisense), 5'-GCCTCCTAAAATGACACGTTG. (SEQ ID NOS: 5-8, respectively.) All PCR products were purified and sequenced directly using the AmpliCycle sequencing kit (Perkin-Elmer, Foster City, Calif.). The sequencing primers were: 5'-GCCACAGTACACGAACCTGG, 5'-CGTGGTCT-GTGTTATAGGGAC, 5'-TGTCCTTCCAGCAGTCGAGC, 5'-AAAAGCTGAGCACGTCACGG, 5'-CTTCACCAC-CTCCGTGACGT, 5'-AGGTTGGCACTGAATTCACGA, 5'-AAAATTGGACGGCGGTTCAT, 5'-GTGATGGTAC-GAAGCGCCC, and ACGGGCGCTTCGTACCAT. (SEQ ID NOS: 9-17, respectively) Mutation analysis for p53 gene was performed as described previously[25].

Northern Analysis

For primary tissues, the collected samples were grossly dissected, quickly frozen or lysed immediately in the guanidine buffer and the RNA was isolated using a CsCl gradient method. For cancer cell lines, total RNA was isolated using the Trizol reagent (GIBCO BRL, Bethesda, Md.). All cell lines except FADU and SaOs2 were established in our laboratory. Northern blot hybridization using the cDNA probes was performed as described[26].

FISH Analysis

FISH was performed as previously described[27]. Specifically, 4 μm thick sections were cut out and mounted on silanized glass slides, fixed in a methanol and glacial acetic acid (3:1) solution for 5 min and then dehydrated in ethanol series and allowed air dry. Cell lines were fixed in the same fixative described above and dropped onto silanized glass slides. Samples were denatured in 70% formamide and 2×SSC at 75° C. for 5 min, followed by dehydration in cold ethanol. The BAC probe containing p40 was isolated as described[8] and was labeled by nick translation with digoxigenin-11-dUTP (Boehringer Mannheim, Indianapolis, Ind.) and the biotin-labeled centromere probe for chromosome 3 was purchased (Vysis, Downers Grove, Ill.). The hybridization mixture consisted of 10% dextran sulfate, 50% formamide, 2×SSC, 0.1 μg of the labeled probe, 10 μg of Cot-1 DNA (GibcoBRL, Gaithersburg, Md.) and 10 μg of salmon sperm DNA. Before hybridization, the mixture was denatured at 75° C. for 5 min and allowed to pre-anneal at 37° C. for 15 min. The probes were hybridized overnight to denatured tissue sections at 37° C. After hybridization, slides were washed for 5 min with 0.5×SSC at 72° C. and then incubated with rhodamine-anti-digoxigenin and FITC-avidin (Oncor, Gaithersburg, Md.). The samples were counterstained with 2-phenylindole-dihydrochloride and examined under a Zeiss Axiophot epi-fluorescent microscope. Tumor areas were determined by evaluating the hematoxylin and eosin stained adjacent sections. Up to 20 nuclear signals were counted under a double-band pass filter. FISH on normal specimens or non-malignant areas was analysed in the same manner as a control. For documentation, images were captured by a CCD camera (Photometrics, Tucson, Ariz.) and processed using the Oncor Image analysing system.

1. Immunohistochemical Analysis

Six micron sections were made from paraffin tissue blocks and the slides were dried at 60° C. for 30 min, treated with xylenes, and then dehydrated in alcohol. Endogenous peroxidase was blocked with 0.3% H202. After blocking with normal goat serum, the slides were incubated with the polyclonal rabbit antiserum against p40 at 1:1000 dilution for 1 hr at room temperature. P40 antiserum was made and provided by David Hill in Oncogene Research Products (Cambridge, Mass.) using a p40 specific peptide (ENNAQTQFSEPQY). A Vectastain ABC Kit and DAB Substrate Kit (Vector, Burlingame, Calif.) were used to visualize the antibody binding.

Figure 3:
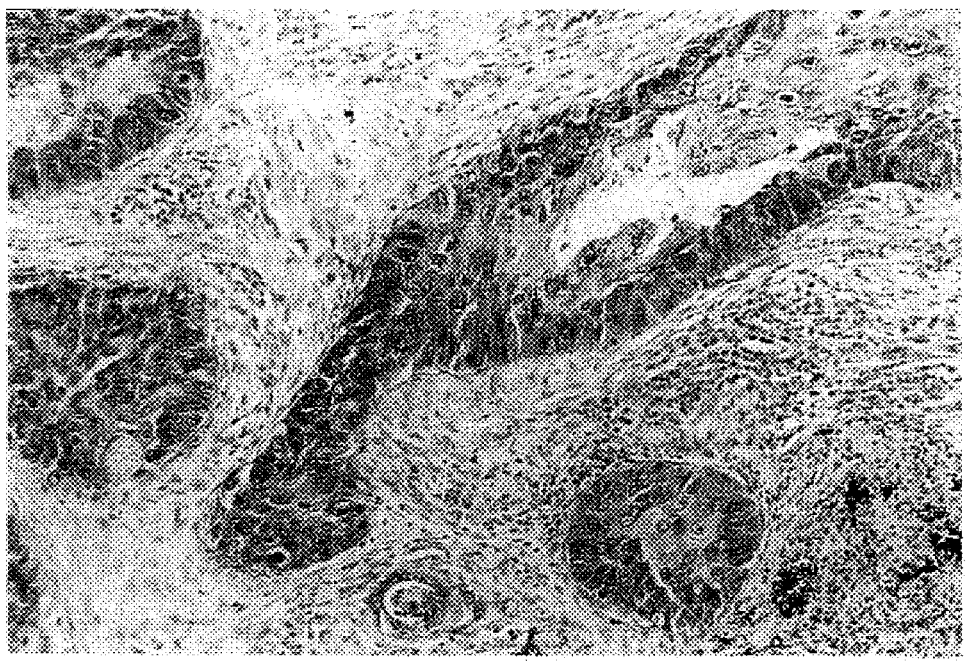
FIG. 3 p40 immunoreactivity in squamous cell carcinoma of the lung (T1). Nests of infiltrating tumor cells demonstrate intense nuclear staining (arrow) after incubation with a polyclonal p40 antibody with absence of expression in surrounding normal cells. This tumor had genomic amplification of p40 and a p53 mutation (Table 2).

Immunohistochemical analysis for p40 was interpreted by an experienced pathologist (W. H. W.) to determine p40 positive and negative staining cases. Only nuclear staining was interpreted as positive (FIG. 3). For control studies, HNSCC cell line (22) and lung cancer cell line (H1299) were used as positive and negative controls. The p40 status of these two cell lines was confirmed by Northern analysis. Optimized conditions were then used for the immunostaining of primary lung cancer specimens.

EXAMPLE 3

Transformation by p40

Figure 4:
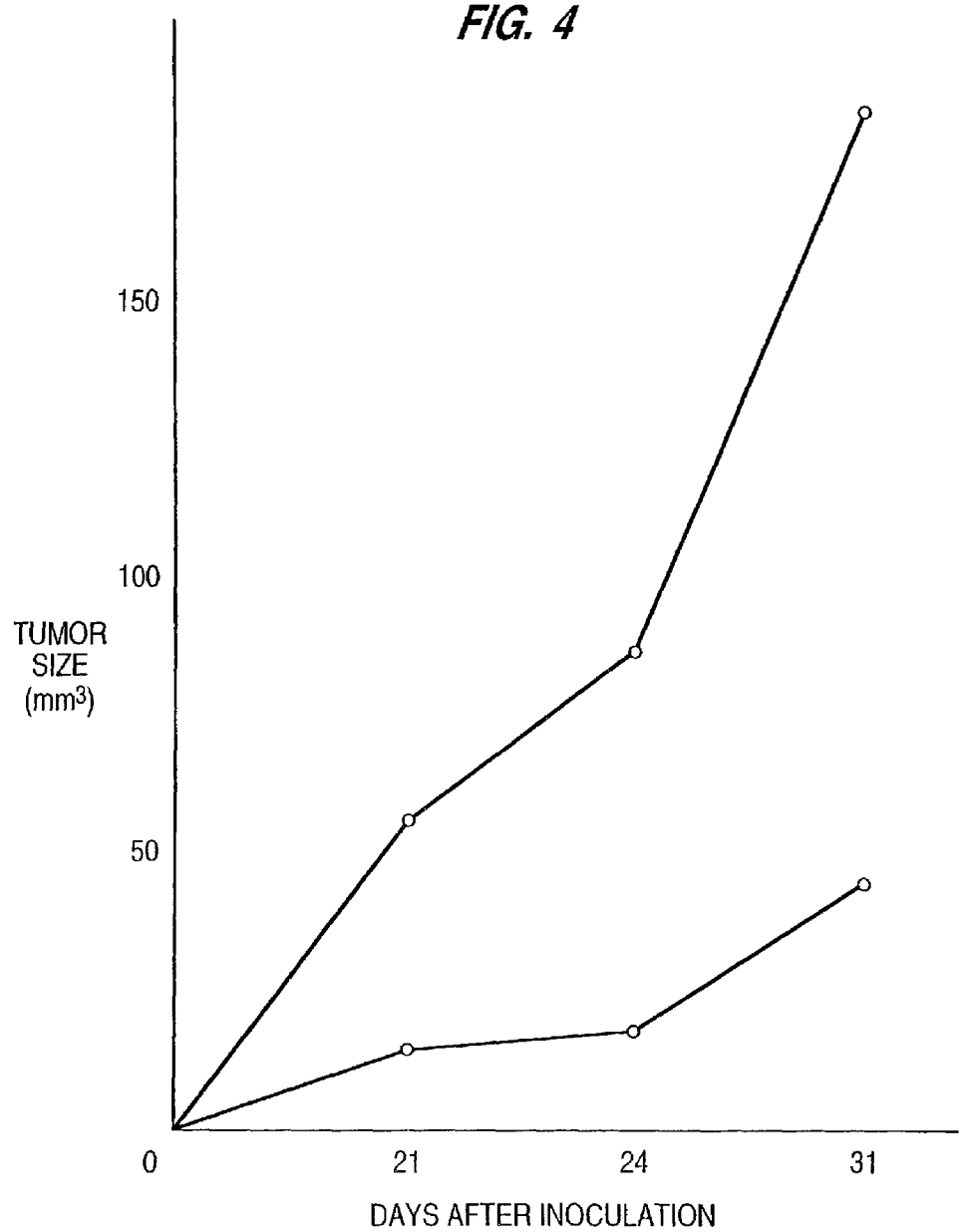
FIG. 4 Tumor growth in nude mice. Rat 1a-p40 cells developed into significantly larger tumors compared with Rat 1a-no cells at day 21 ($p=0.0335$, t-test), day 24 ($p=0.0445$), and day 31 ($p=0.0009$). Each curve represents the average volume of 5 tumors as shown (Methods). On day 31, Rat 1a-p40 tumors averaged $184.2\pm49.6$ mm$^3$ while Rat 1a-no tumors averaged $47.2\pm33.1$ mm$^3$ in size.

Clones that overexpress p40 (Rat 1a-p40) and vector only controls (Rat-1a-no) were generated by plasmid transfection into a parental Rat 1a fibroblast cell line. The transformed phenotype of these cell lines was initially assayed by culture in soft agar. Rat 1a-p40 cells displayed a significantly increased frequency of colony formation and larger colonies compared with Rat 1a-no cells (Table 3). Pooled clones overexpressing p40 were inoculated into nude mice to examine the tumorigenicity of p40 in vivo. Tumor size was measured at 21, 24, and 31 days after inoculation, and we found that Rat 1a-p40 cells produced significantly larger tumors compared with Rat 1a-no cells (FIG. 4). These observations suggest that p40 overexpression results in a transformed phenotype and further supports p40's role as an oncogene.

TABLE 3

The number of colonies in soft agar plates from transfected Rat 1a cells

| size of colonies (μm) | 200-400 | 400+ |
|---|---|---|
| Rat 1a-p40 | 695 ± 65 | 37 ± 16 |
| Rat 1a-no | 363 ± 125 | 9 ± 4 |
| p (t-test) | 0.0150 | 0.0384 |

Transformation Assay

A full length p40 cDNA was cloned into pCEP4 (Invitrogen, Carlsbad, Calif.). pCEP4-p40 and pCEP4 were transfected to Rat 1a fibroblast cells using Lipofectamine (GibcoBRL, Gaithersberg, Md.) according to the protocol provided by the manufacturer. Cells were selected with the Hygromycin B at 200 μg/ml and P40 expression in Rat 1a-p40 cells was confirmed by immunohistochemistry.

For soft agar analysis, $10^5$ cells of either Rat 1a-p40 or Rat 1a-no in twofold-concentrated DMEM-20% fetal bovine serum were mixed with an equal volume of 0.8% agarose and poured onto a bed of 0.7% agarose. After 18 days, colonies were counted and measured under the microscope. All experiments were performed in triplicate and differences were analysed by the t-test.

Tumor growth in nude mice was assayed by innoculating $5 \times 10^6$ cells of either Rat 1a-p40 or Rat 1a-no into the right or left frank of 5 nude mice respectively. At 21 and 24 days after inoculation, tumor size was measured in 3 dimensions. Differences of tumor volumes were analysed by the t-test.

EXAMPLE 4 p40 Displays a Dominant Negative Effect on p53 Transcriptional Activity

Based on its structural similarity, p40 may compete for p53 binding sites and alter the ability of p53 to regulate target genes. Previous reports had suggested that ΔNp63, similar to p40 in that it lacks an N-terminal domain, could bind to p53 target sites in a competitive manner and decrease p53 transactivation[10]. We thus co-infected SaOs2 cells with a constant amount of p53 adenovirus (MOI=2) and varying concentrations of p40 adenovirus (MOI=0.5 to 4), and assayed for transactivation on a consensus p53 promoter (PG13) driving the luciferase reporter gene[3]. As seen previously, at an equal ratio of p53 to p40, transactivation activity was reduced by about 50% compared to p53 alone (data not shown).

Luciferase Assay p40 and p53 adenoviruses were co-infected into SaOs2 cells for 1 hr at the indicated ratios. After the infection, the same amount of plasmid containing PG13 luciferase reporter gene was transfected to these SaOs2 cells using Lipofectamine (GibcoBRL, Gaithersberg, Md.) according to the protocol provided by the manufacturer. The PG13 luciferase reporter gene contains 13 tandem repeats of a p53 binding sequence upstream of the luciferase reporter gene. Cells were lysed 18 hr after transfection and luciferase activity was detected using the Luciferase Assay System (Promega, Madison, Wis.). All luminescence values were measured on a LS60001C Liquid Scintilation System (Beckman, Fullerton, Calif.).

EXAMPLE 5 p40 Displays a Dominant Negative Effect on p53 Transcriptional Activity

Based on its structural similarity, p40 may compete for p53 binding sites and alter the ability of p53 to regulate target genes. Previous reports had suggested that ΔNp63, similar to p40 in that it lacks an N-terminal domain, could bind to p53 target sites in a competitive manner and decrease p53 transactivation[10]. We thus co-infected SaOs2 cells with a constant amount of p53 adenovirus (MOI=2) and varying concentrations of p40 adenovirus (MOI=0.5 to 4), and assayed for transactivation on a consensus p53 promoter (PG13) driving the luciferase reporter gene[3]. As seen previously, at an equal ratio of p53 to p40, transactivation activity was reduced by about 50% compared to p53 alone (data not shown).

EXAMPLE 6 p40 Interacts with p53

Figure 5:
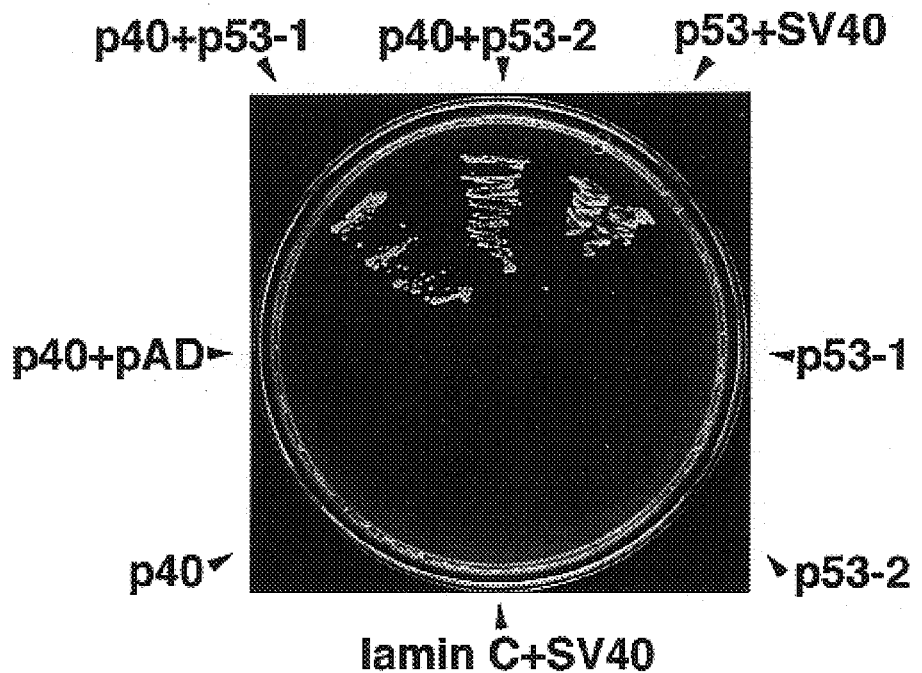
FIG. 5 Two-hybrid yeast expression analysis of interaction of p40 with p53. *Saccharomyces cerevisiae* (strain SFY526) were co-transformed by the lithium acetate method with pGal4-BD-p40 (alone), pGal4-AD-p53-1 (alone), pGal4-AD-p53-2 (alone) or with various combinations of pGal4-BD-p40 and pGal4-AD-p53-1, or pGal4-AD-p53-2, or pGal4-AD. As controls, yeast were co-transformed with control plasmids (pGal4-BD-p53 with pGal4-AD-SV40, or pGal4-BD-lamin C with pGal4-AD-SV40). First, transformed yeast were selected on double drop-out agar plates (Trp−/Leu−). Then colonies obtained from each group were re-streaked on new triple drop-out agar plates (Trp−/Leu−/His−). After 3 day incubation final plates were photographed demonstrating growth of yeast with the two p53+p40 clones and the control p53+SV40 clone.

In order to further understand the function of p40, a yeast two-hybrid screen using p40 as a bait was undertaken. We screened $1.6 \times 10^6$ clones from a mouse embryonic cDNA library for genes encoding proteins that were able to bind p40 specifically. Twenty-one clones that specifically activated the HIS3 and LacZ reporter genes in the presence of p40 were analysed. After sequence analysis and database comparisons of these 21 clones, the most common target protein identified was p53, yielding 3 independent, partially overlapping clones (FIG. 5).

The strength of this interaction is summarized in Table 4. The interaction between 2 of the identified p53 clones was consistent as measured by β-galactosidase activity and was nearly as strong as the interaction between p53 and the SV40 positive control. Examination of the region of overlap within the clones identified the DNA binding domain as the probable interaction motif.

TABLE 4

The strength of the interaction between bait and prey

| Bait | Prey | Trp+ | Leu+ | His+ |
|---|---|---|---|---|
| β-galactosidase (nmole/min/mg) | | | | |
| pGal4-BD-p53 | pGal4-AD-SV-40 | + | + | + | 65.3 ± 6.3 |
| pGal4-BD-laminC | pGal4-AD-SV-40 | | + | + | -2.6 ± 0.9 |
| pGal4-p40 | | + | - | - | 3.7 ± 1.2 |
| pGal4-p40 | pGal4-AD | + | + | - | 4.2 ± 1.1 |
| pGal4-AD-p53-1 | | - | + | + | -3.3 ± 0.8 |
| pGal4-AD-p53-2 | | | - | + | -3.4 ± 0.5 |
| pGal4-BD-p40 | pGal4-AD-P53-1 | + | + | + | 33.6 ± 3.7 |
| pGal4-BD-p40 | pGal4-AD-p53-2 | + | + | + | 31.8 ± 2.9 |

Yeast Two-hybrid Screen

To screen for potential binding partners of p40, we employed a yeast two-hybrid system and screened the Hybri-Zap-Gal4 mouse embryonic cDNA library (#977317, mouse strain B6:C57BL/6, day 14.5, Stratagene, LaJolla, Calif.). To prepare the bait plasmid, human p40 cDNA was inserted 3′ to the cDNA for the Gal4 binding domain of plasmid pGal4-BD (Stratagene, Calif.). The resultant pGal4-BD-p40 bait plasmid encoded a fusion protein comprised of the Gal4 binding domain and a p40 protein. YRG-2 yeast cells were co-transformed with the pGal4-BD-p40 bait plasmid and a Hybri-Zap-Gal4-based library, and then grown on a selective medium lacking tryptophan, leucin and histidine or combinations thereof. Colonies that contained a cDNA encoding target library proteins interacting with the bait fusion protein were identified by the assay based on activation of transcription of the yeast chromosomal HIS3- and lacZ-genes (filter-lift assay). A total of $1.6 \times 10^6$ yeast transformants were placed under Trp-Leu-His- selection. Plasmid preparations from β-gal positive yeast colonies were isolated and re-transformed into library-efficiency competent *E. coli* DH5α cells.

The ampicillin resistant colonies were then grown up and DNA preps were analysed by EcoRI/XhoI restriction mapping followed by DNA sequencing. To ensure that cDNA clones obtained from the first screen encoded true positive p40-interactors, we introduced pGal4-BD-p40 and pGal4-AD-clones into *Saccharomyces cerevisiae* (strain SFY 526) together and separately, as well as with positive and negative control pairs (pGal4-BD-p53 plus pGal4-AD-SV-40, and pGal4-BD-lamin C plus pGal4-AD-SV-40, respectively). Yeast colonies were grown up in agar-agar plates lacking tryptophan, leucin or tryptophan plus leucine and then growing colonies were transferred into agar-agar plates lacking tryptophan, leucine and histidine. Yeast colonies that were grown on latter plates were subjected to quantitative liquid β-galactosidase activity assay using o-nitrophenyl-β-D-galactopyranoside (OPNG) as a substrate (nmol OPNG cleaved/min/mg protein measured at OD420)[28].

The invention claimed is:

1. An isolated preparation of antibodies which specifically bind to a p40 protein as shown in SEQ ID NO:2 wherein the antibodies bind to an epitope in peptide ENNAQTQFSEPQY (residues 5-17 of SEQ ID NO: 2), wherein the antibodies are monoclonal.

2. An isolated preparation of antibodies which specifically bind to a p40 protein as shown in SEQ ID NO: 2 wherein the antibodies were generated using as an immunogen a peptide consisting of sequence ENNAQTQSEPQY (residues 5-17 of SEQ ID NO: 2), wherein the antibodies are monoclonal.

3. An isolated preparation of antibodies which specifically bind to an epitope in peptide ENNAQTQFSEPQY (residues 5-17 of SEQ ID NO: 2), wherein the antibodies are monoclonal.

* * * * *